(12) United States Patent
Sullivan et al.

(10) Patent No.: US 12,057,213 B2
(45) Date of Patent: Aug. 6, 2024

(54) NEUROMODULATION AND ASSOCIATED SYSTEMS AND METHODS FOR THE MANAGEMENT OF PAIN

(71) Applicant: Medtronic Ireland Manufacturing Unlimited Company, Dublin (IE)

(72) Inventors: Carol Sullivan, Litchfield Park, AZ (US); Neil Barman, Menlo Park, CA (US); Dwayne S. Yamasaki, St. Augustine, FL (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 58 days.

(21) Appl. No.: 18/045,556

(22) Filed: Oct. 11, 2022

(65) Prior Publication Data
US 2023/0057437 A1  Feb. 23, 2023

Related U.S. Application Data

(63) Continuation of application No. 16/988,068, filed on Aug. 7, 2020, now Pat. No. 11,515,029, which is a
(Continued)

(51) Int. Cl.
*G16H 20/30* (2018.01)
*A61B 5/00* (2006.01)
(Continued)

(52) U.S. Cl.
CPC ........... *G16H 20/30* (2018.01); *A61B 5/4824* (2013.01); *A61B 18/0206* (2013.01); *A61F 7/12* (2013.01);
(Continued)

(58) Field of Classification Search
CPC ............ A61B 18/0206; A61B 18/1492; A61B 2018/0022; A61B 2018/00345; A61B 2018/00434; A61B 2018/00791; A61B 2018/00839; A61B 2018/0212; A61B 2018/0262; A61B 5/02405; A61B 5/14503; A61B 5/4035; A61B 5/4824;
(Continued)

(56) References Cited

U.S. PATENT DOCUMENTS

2010/0010567 A1* 1/2010 Deem .................. A61N 1/0492
607/46

* cited by examiner

Primary Examiner — Mark D Remaly
(74) Attorney, Agent, or Firm — Shumaker & Sieffert, P.A

(57) ABSTRACT

Methods for treating and managing pain in a patient with therapeutic neuromodulation and associated systems and methods are disclosed herein. Chronic or debilitating pain can be associated, for example, with a disease or condition of the abdominal or reproductive viscera. One aspect of the present technology is directed to methods that at least partially inhibit sympathetic neural activity in nerves proximate a target blood vessel of a diseased or damaged organ of a patient experiencing pain. Targeted sympathetic nerve activity can be modulated at least along afferent pathways which can improve a measurable parameter associated with the pain of the patient The modulation can be achieved, for example, using an intravascularly positioned catheter carrying a therapeutic assembly, e.g., a therapeutic assembly configured to use electrically-induced, thermally-induced, and/or chemically-induced approaches to modulate the target sympathetic nerve.

20 Claims, 12 Drawing Sheets

Related U.S. Application Data continuation of application No. 14/379,874, filed as application No. PCT/US2013/029547 on Mar. 7, 2013, now Pat. No. 10,737,123.

(60) Provisional application No. 61/608,579, filed on Mar. 8, 2012, provisional application No. 61/608,437, filed on Mar. 8, 2012.

(51) Int. Cl.
| | |
|---|---|
| *A61B 18/02* | (2006.01) |
| *A61F 7/12* | (2006.01) |
| *A61N 2/00* | (2006.01) |
| *A61N 7/00* | (2006.01) |
| *G16H 20/40* | (2018.01) |
| *G16H 50/30* | (2018.01) |
| *A61B 5/024* | (2006.01) |
| *A61B 5/145* | (2006.01) |
| *A61B 18/00* | (2006.01) |
| *A61B 18/14* | (2006.01) |
| *A61F 7/00* | (2006.01) |
| *A61N 1/36* | (2006.01) |
| *A61N 7/02* | (2006.01) |
| *G16H 10/20* | (2018.01) |

(52) U.S. Cl.
CPC ............... *A61N 2/008* (2013.01); *A61N 7/00* (2013.01); *G16H 20/40* (2018.01); *G16H 50/30* (2018.01); *A61B 5/02405* (2013.01); *A61B 5/14503* (2013.01); *A61B 5/4035* (2013.01); *A61B 2018/0022* (2013.01); *A61B 2018/00345* (2013.01); *A61B 2018/00434* (2013.01); *A61B 2018/00791* (2013.01); *A61B 2018/00839* (2013.01); *A61B 2018/0212* (2013.01); *A61B 2018/0262* (2013.01); *A61B 18/1492* (2013.01); *A61F 2007/0056* (2013.01); *A61F 7/123* (2013.01); *A61F 2007/126* (2013.01); *A61N 1/36021* (2013.01); *A61N 2007/0026* (2013.01); *A61N 2007/0043* (2013.01); *A61N 7/02* (2013.01); *A61N 7/022* (2013.01); *G16H 10/20* (2018.01); *Y02A 90/10* (2018.01)

(58) Field of Classification Search
CPC ........ A61F 2007/0056; A61F 2007/126; A61F 7/12; A61F 7/123; A61N 1/36021; A61N 2007/0026; A61N 2007/0043; A61N 2/008; A61N 7/00; A61N 7/02; A61N 7/022; G16H 10/20; G16H 20/30; G16H 20/40; G16H 50/30; Y02A 90/10
See application file for complete search history.

FIG. 1A

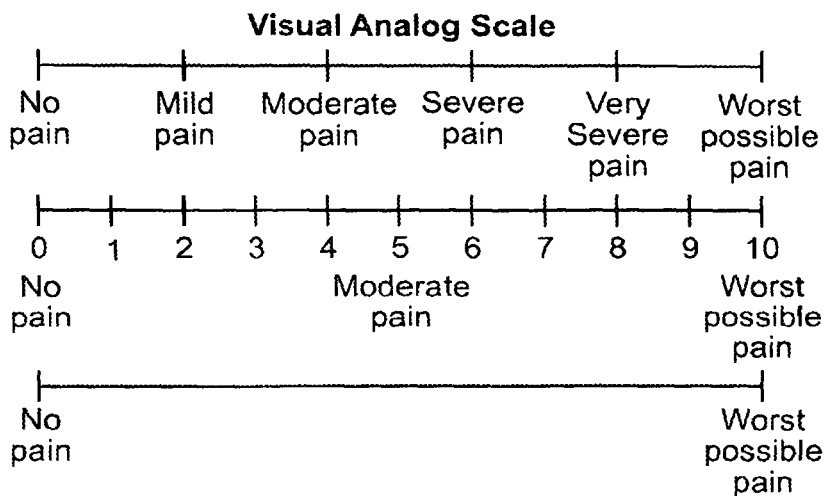

Visual Analog Scale

FIG. 1B

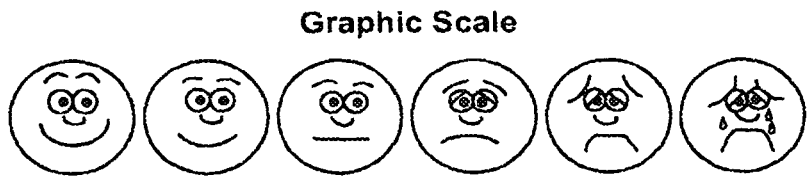

Graphic Scale

FIG. 1C
Word Descriptor Scale

0 = No pain
1 = Mild pain
2 = Distressing pain
3 = Severe pain
4 = Horrible pain
5 = Excruciating pain

FIG. 1D
Verbal Scale

"On a scale of 0 to 10, with 0 meaning no pain and 10 meaning the worst pain you can imagine, how much pain are you having now?"

FIG. 1E
Functional Pain Scale

0 = No pain
1 = Tolerable and pain does not prevent any activities
2 = Tolerable and pain prevents some activities
3 = Intolerable and pain does not prevent use of telephone, TV viewing, or reading.
4 = Intolerable and pain prevents use of telephone, TV viewing, or reading.
5 = Intolerable and pain prevents verbal communication.

*Arterial Vasculature*

*Venous Vasculature*

NEUROMODULATION AND ASSOCIATED SYSTEMS AND METHODS FOR THE MANAGEMENT OF PAIN

CROSS-REFERENCE TO RELATED APPLICATION(S)

The present application is a continuation of U.S. patent application Ser. No. 16/988,068, filed Aug. 7, 2020, and entitled, "NEUROMODULATION AND ASSOCIATED SYSTEMS AND METHODS FOR THE MANAGEMENT OF PAIN," which is a continuation of U.S. patent application Ser. No. 14/379,874, filed Aug. 20, 2014, and entitled. "NEUROMODULATION AND ASSOCIATED SYSTEMS AND METHODS FOR THE MANAGEMENT OF PAIN," which is a 35 U.S.C. § 371 U.S. National Phase application of International Application No PCT/US2013/029547, filed Mar. 7, 2013, and entitled, "NEUROMODULATION AND ASSOCIATED SYSTEMS AND METHODS FOR THE MANAGEMENT OF PAIN," which claims priority to and the benefit of U.S. Provisional Patent Application No. 61/608,579, filed Mar. 8, 2012, entitled "NEUROMODULATION FOR PANCREATIC PAIN MANAGEMENT AND ASSOCIATED SYSTEMS AND METHODS," and U.S. Provisional Patent Application No. 61/608,437, filed Mar. 8, 2012, entitled "TESTICULAR AND/OR PENILE NEUROMODULATION AND ASSOCIATED SYSTEMS AND METHODS," both all of which are incorporated herein by reference in their entireties.

TECHNICAL FIELD

The present technology relates generally to pain management using neuromodulation and associated systems and methods.

BACKGROUND

Patients with hepatobiliary diseases (e.g., diseases of the liver, gallbladder and biliary tract), conditions of the pancreas (e.g., chronic pancreatitis, pancreatic cancer), and visceral artery insufficiency can all suffer from chronic and/or intractable pain. Such pain associated with these conditions, for example, can be both debilitating and difficult to treat. Typically, analgesics and/or narcotics are used to manage the patient's pain; however, conventional pain-management medications (e.g., opiates) are often ineffective or only partially effective and can cause undesirable side effects and dependency. Conventional non-pharmacological treatments for the treatment of conditions of the pancreas, for example, can include locally injecting anesthetic drugs or nerve-destroying agents (e.g., alcohol) to reduce nerve signaling through the celiac ganglia and/or celiac plexus. This procedure, known as a "celiac plexus block," can be effective in some cases, but its effectiveness tends to diminish over time. For example, the procedure must typically be repeated every three to four months for sustained pain management. Furthermore, executing a conventional celiac plexus block involves inserting a needle through the gastrointestinal, intraabdominal and/or retroperitoneal anatomy to a position proximate the celiac plexus. This manner of accessing the celiac plexus can be imprecise and can have a variety of serious potential complications, include retroperitoneal hemorrhage, spinal-cord puncture, and paraplegia. Accordingly, there is a need for alternative treatments.

Chronic pain can also be associated with both male and female reproductive/genital organs. For example, orchialgia is a condition characterized by long term testicular pain that often has no known etiology but can in some cases be caused by injury, infection, surgery, cancer or testicular torsion and can be a possible complication after vasectomy. Vulvodynia is a condition characterized by chronic pain affecting the vulvar area and often occurs without an identifiable cause or visible pathology. Both orchialgia and vulvodynia are treated, for example, with anti-inflammatory medications or other pain medications, antidepressants (e.g., nortriptyline, amitriptyline), and anti-anxiety drugs; however, these are not always effective and can have undesirable side effects. Intractable cases of orchialgia can be treated with microsurgical denervation of the spermatic cord; however, the procedure has several potential complications (e.g., testicular atrophy, hydrocele, hypoesthesia of the scrotum, penile shaft, inguinal or medial thigh skin, and persistent testicular pain). Intractable cases of vulvodynia can be treated with injection or surgical destruction of the pudendal nerve; however, the procedure has several potential complications (e.g., permanent vulva numbness, continued vulvodynia pain, etc.). Accordingly, there is a need for alternative treatments.

Pain signals travel along various neural pathways through the body, including the sympathetic nervous system (SNS). The SNS is a primarily involuntary bodily control system typically associated with stress responses. Fibers of the SNS extend through tissue in almost every organ system of the human body. For example, some efferent SNS fibers extend from the brain, intertwine along the aorta, and branch our to various organs. Likewise, afferent nerve fibers traveling with SNS nerve fibers can transmit signals, including pain signals, from the organs (e.g., abdominal organs, reproductive/genital organs) to the brain.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIGS. 1A-1E illustrate various examples of pain scales that can be used to quantify or qualify pain as it is occurring and in accordance with an embodiment of the present technology.

DETAILED DESCRIPTION

Figure 2A:
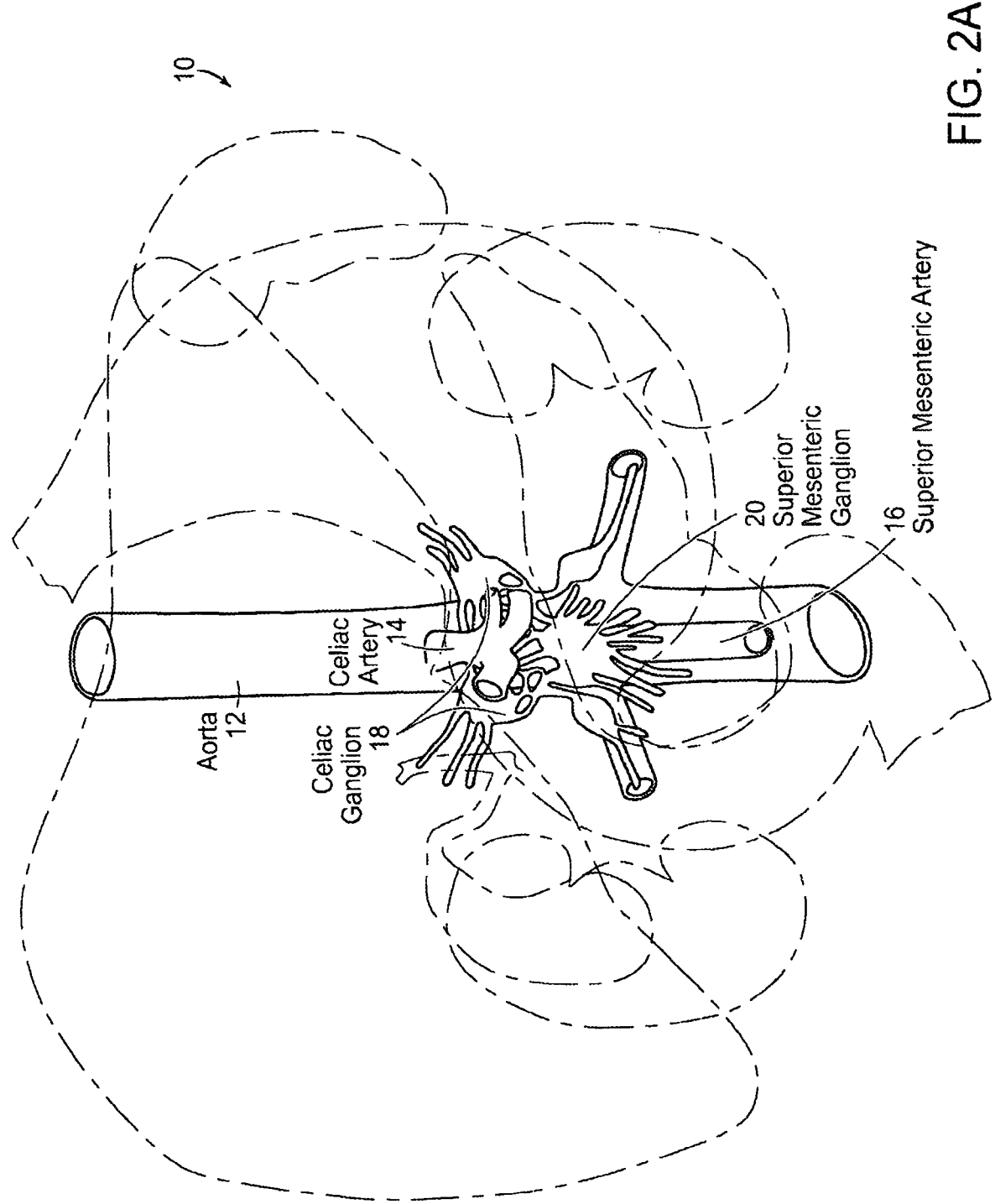
FIGS. 2A-2B are anatomical views illustrating the abdominal viscera and the nearby nerve structures and vessels.

The present technology is generally directed to modulation of one or more nerve structures associated with abdominal viscera (e.g., stomach, intestine, liver and biliary system, pancreas, spleen, kidneys, ureters, and suprarenal glands) and/or reproductive organs to reduce perceived pain associated with conditions or diseases of these physiological structures. For example, several embodiments are directed to modulation of at least a portion of the superior mesenteric plexus, the celiac plexus, and/or the hepatic plexus to reduce pain associated with conditions of the pancreas, the liver or other abdominal organ systems. Other embodiments are directed to modulation of sympathetic nerves innervating male and female reproductive/genital organs to reduce perceived chronic pain associated with conditions or diseases associated with the testes (e.g., orchialgia) and/or penis (e.g., injury, Peyronie's disease) as well as the vulva, vagina, and/or clitoris to reduce perceived chronic pain associated with conditions or diseases associated with the female reproductive system (e.g., vulvodynia). For example, some embodiments are directed to modulation of at least a portion of the testicular and/or penile sympathetic nerves (e.g., sympathetic nerves along the testicular vessels, pudendal vessels or other associated structures), and/or to modulation of at least a portion of the spermatic plexus, the lumbar plexus, the sacral plexus, the uterovaginal plexus and/or particular sympathetic nerves innervating the testes, penis, vulva, vagina, and/or clitoris (e.g., perineal nerve, ilioinguinal nerve, genitofemoral nerve, pudendal nerve).

In many embodiments, modulation of targeted nerves and nerve structures can include modulation of the nerves in locations proximate (e.g., at or near) a percutaneously accessible artery (e.g., superior mesenteric artery, the celiac artery) or vein (e.g., superior mesenteric vein) and/or other suitable structures. As discussed in greater detail below, neuromodulation of one or more nerve structures associated with the abdominal organs (e.g., pancreas, liver, gallbladder) or associated with reproductive organs (e.g., testes, penis, vulva, vagina, uterus, ovaries, etc.) can include rendering neural fibers inert, inactive, or otherwise completely or partially reduced in function. This result can be electrically-induced, thermally-induced, or induced by another mechanism (e.g., chemically-induced) during a neuromodulation procedure, e.g., a procedure including percutaneous transluminal intravascular access.

Specific details of several embodiments of the technology are described below with reference to FIGS. 1A-9. The embodiments can include, for example, modulating nerves proximate (e.g., at or near) the superior mesenteric artery, the inferior mesenteric artery, the celiac artery or one of its branches, the superior mesenteric vein, the internal pudendal artery, a testicular artery and/or other suitable structures. Although many of the embodiments are described herein with respect to electrically-induced, thermally-induced, and chemically-induced approaches, other treatment modalities in addition to those described herein are within the scope of the present technology. Additionally, other embodiments of the present technology can have different configurations, components, or procedures than those described herein. A person of ordinary skill in the art, therefore, will accordingly understand that the technology can have other embodiments with additional elements and that the technology can have other embodiments without several of the features shown and described below with reference to FIGS. 1A-9.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

I. Chronic Pain

Nociceptive pain (e.g., caused by activation of nociceptors) can be considered chronic if it extends beyond an expected healing duration. Chronic pain originating in the viscera (organs) can be localized, but often can be difficult to locate as several visceral regions produce "referred" pain when damaged or inflamed (e.g., where sensation is located in an area distant from the site of pathology or injury). In addition to reduced quality of life and discomfort, chronic pain of varying etiologies can affect brain structure and function. For example, magnetic resonance imaging studies have shown abnormal anatomical and functional connectivity in areas of the brain relating to pain processing and persistent pain has been shown to cause grey matter loss, which is reversible once pain is resolved. Additionally brain activity in patients suffering from chronic pain (e.g., measured by electroencephalogram) has been demonstrated to be altered, suggesting point-induced neuroplastic changes. Chronic pain is associated with higher rates of depression, anxiety, sleep disturbance and insomnia due to medications and underlying disease symptoms.

Pharmacologic management of pain is commonly used to alleviate both discomfort and other sequalae of chronic pain, particularly chronic pain associated with conditions and diseases of the abdominal viscera (e.g., pancreas, gallbladder, liver, stomach, intestines, etc.) and the reproductive system (e.g., testes, vulva, etc.). Pain medication can include, for example, analgesia (e.g., acetaminophen, salicylic acid, non-steroidal anti-inflammatory drugs, opioids, COX-2 inhibitors) alone or in combination with other agents (e.g., anesthetics, antidepressants, antiepileptics, narcotics, etc.).

For some conditions, specialized procedures are used to treat pain, such as administering nerve blocks or microsurgical techniques to damage or occlude nerves. For example, a celiac ganglia/plexus nerve blocking procedure includes guided injections, e.g., of drugs (e.g. steroids, anesthetics), or nerve-destroying (e.g. alcohol), or nerve-blocking (e.g. onabotulinumtoxinA) agents, to reduce nerve signaling through the celiac ganglia/plexus for the treatment of intractable pain from cancers, such as pancreatic cancer, or from chronic pancreatitis. Access to the celiac nerves via (1) X-ray computed tomography (CT) guided needle through the skin or (2) endoscopic catheters delivered through the gastrointestinal tract can be used to deliver combination of long-acting anesthetics, steroids, or onabotulinumtoxinA (sold under the trademark BOTOX), or to deliver alcohol or other neutrally destructive agents for destroying nerve fibers.

Nerve blocking and microsurgical techniques appear to be able to alleviate pain for 3-4 month durations in some patients; however, the techniques have limited efficacy, and can pose undesirable risks (e.g., paraplegia, damage to nearby structures, etc.). Prescribed pain medication therapies are also limited in their efficacy as they are often not able to control pain in the setting of hepatobiliary diseases, chronic pancreatitis, pancreatic cancer, and visceral artery insufficiency, as well as in some conditions of the reproductive organs, such as orchialgia and vulvodynia.

A patient suspected of having chronic, debilitating or intractable pain or having one or more positive diagnosis of a condition or disease associated with chronic pain, can be evaluated for pain level and level of function. Pain evaluation can include capturing features such as quality (e.g., burning, cramping, aching, deep, superficial, boring, shooting, etc.), severity, location, radiation pattern, duration, timing (e.g., including pattern and degree of fluctuation and frequency of remissions), and exacerbating and relieving factors. Additionally, pain evaluation can also assess aspects of pain relating to a patient's level of functioning, for example, by focusing on activities of daily living (e.g., dressing, bathing), employment, avocations, and personal relationships (e.g., sexual activity/ability). Use of pain measurement scales can assist in the evaluation process by measuring a patient's pain intensity and/or functionality, for example. Pain scales, as well as other data that can be collected in a pain evaluation of a patient, are based on self-report, observational (behavioral), or physiological data. Self-report is considered the primary form and common for children, adolescents, adults and seniors who are able to communicate; however, additional pain scales are also available for neonates, infants, and other persons whose communication is impaired. FIGS. 1A-1E illustrate various examples of pain scales that can be used to quantify pain as it is occurring. For example, an adult patient can be assessed using a standardized Visual Analog Scale (VAS) where patients are instructed to mark a line anchored with terms describing the extremes of pain intensity (FIG. 1A). Operationally, the VAS is usually a horizontal line, 100 mm in length, anchored by word descriptors at each end. The patient marks on the line the point that they feel represents their perception of their current state. The VAS score is determined by measuring in millimeters from the left hand end of the line to the point that the patient marks. The position of the patient's marking is then translated into a score from 1 to 10. Other types of pain scales for children might include a graphic faces pain scale, Wong-Baker FACES Pain Rating Scale (FIG. 1B), a colored analogue scale, or an observational scale such as a Face Legs Arms Cry Consolability Scale (FLACC). Other types of scales, such as a word descriptor scale (FIG. 1C), a verbal scale (FIG. 1D) and a Functional pain scale (FIG. 1E) can also be used alone or in conjunction with other pain measurement scales or assessment tools to quantify pain.

A. Conditions and Diseases of the Abdominal Viscera

The abdominal viscera can include, for example, the stomach, intestine, liver and biliary system, pancreas, spleen, kidneys, ureters, and suprarenal glands. Several embodiments described herein address chronic and/or otherwise intractable pain associated with conditions or diseases of these abdominal organs. For example, pain associated with conditions of the pancreas (e.g., pancreatic cancer and pancreatitis) can be debilitating and difficult to treat. Pancreatic cancer is characterized by malignant tumors (e.g., adenocarcinomas) within the pancreas. Pancreatic cancer is commonly diagnosed at late stage in patients after presentation of symptoms such as abdominal pain, lower back pain and/or jaundice. Prognosis is poor and pain management is typically necessary for pancreatic cancer patients to improve quality and life expectancy. Pancreatitis is the inflammation of the pancreas that occurs when pancreatic enzymes (e.g., trypsin) that digest food are activated in the pancreas instead of the small intestine. Pancreatitis can be acute (e.g., begin suddenly and last a few days or weeks) or chronic (e.g., occur over many years). The most common symptoms of pancreatitis are upper abdominal burning pain radiating to the back, nausea and vomiting that worsens with eating. Chronic pancreatitis can lead to diabetes or pancreatic cancer. Diagnosis is based on characteristic abdominal pain that can be severe, elevated blood amylase or lipase levels, and abdominal ultrasound. Pain management (e.g., with the use of analgesics) along with dehydration control are the primary treatments, with chronic pancreatitis requiring long-time use of pain medications, including opiates (e.g., morphine).

Hepatobiliary diseases affect the liver and/or biliary tract and can include, for example, hepatitis, other infectious diseases (e.g., toxoplasmosis, syphilis, Epstein-Barr virus, yellow fever, rubella, leptospirosis, etc.), alcoholic liver disease, toxic liver disease, fatty liver disease, liver tumors, metabolic diseases (e.g., hemochromatosis, Gilbert's syndrome, etc.), vascular disorders (e.g., Budd-Chiari syndrome), liver abscess or cysts, malignant neoplasm of the gallbladder or other parts of the biliary tract, gallstones, cholecystitis, and gallbladder obstructions among other conditions. Many of these conditions and diseases are associated with pain, particularly intractable abdominal pain requiring pain management treatment with analgesics.

In addition to the above conditions and diseases of the abdominal viscera, other abdominal organs or structures can also be associated with chronic pain, such as, for example, conditions of the spleen (e.g., inflammation, enlarged spleen due to mononucleosis, leukemia, lymphoma, Hodgkin's disease, etc.) and stomach (e.g., cancer), and the small intestine and colon (e.g., cancer, untreatable chronic ischemia). In other embodiments, patients can also suffer from chronic pain associated with, for example, diseases and conditions associated with the peripheral vasculature (e.g., ischemia, claudication), complex regional pain syndrome (e.g., reflex sympathetic dystrophy), Raynaud's syndrome, and scleroderma.

B. Conditions and Diseases of the Reproductive System and Pelvic Region

The male reproductive system includes the reproductive organs necessary for sperm production and storage (e.g., testes, scrotum, and epididymis), ejaculatory fluid producing glands (e.g., seminal vesicles, prostate, and vas deferens), and reproductive organs used for copulation and deposition of sperm (e.g., penis, urethra, vas deferens, and Cowper's gland). Several embodiments described herein address chronic and/or otherwise intractable pain associated with conditions or diseases of these male reproductive organs. For example, orchialgia is a condition characterized by long term testicular pain caused by injury, infection, surgery, cancer or testicular torsion and can be a possible complication after vasectomy. Orchialgia is treated, for example, with NSAIDs or other pain medications; however, these are not always effective and can have undesirable side effects. Intractable cases of orchialgia can be treated with microsurgical denervation of the spermatic cord; however, the procedure has several potential complications (e.g., testicular atrophy, hydrocele, hypoesthesia of the scrotum, penile shaft, inguinal or medial thigh skin, and persistent testicular pain). Varicocele is an abnormal enlargement of the pampiniform venous plexus in the scrotum which can cause a dragging-like or aching pain within the scrotum.

The female reproductive system includes the uterus which hosts developing fetuses, produces vaginal and uterine secretions and provides a path for male sperm to the fallopian tubes, and includes the ovaries which produce the eggs. The uterus connects to the external genitalia (e.g., the labia, clitoris and urethra) through the vagina which is attached to the uterus through the cervix. Several embodiments described herein address chronic and/or otherwise intractable pain associated with conditions or diseases of these female reproductive organs and genitalia. For example, vulvodynia is a condition characterized by chronic pain affecting the vulvar area and often occurs without an identifiable cause or visible pathology. Possible causes of vulvodynia can be inflammation, allergy, autoimmune disorder, infection, injury and neuropathy (e.g., including an increased number of nerve ending is the vaginal area), results of genital surgery or pelvic floor dysfunction. In many cases, specific causes of vulvodynia are often elusive; however, pain is the most notable symptom and can be characterized as a burning, stinging, irritation or sharp pain that occurs in the vulva, including the labia and the entrance to the vagina. Vulvar Vestibulitis Syndrome (VVS) is vulvodynia located to the vestibular region, while clitorodynia is pain that extends into the clitoris. Vulvodynia is often treated, for example, with topical creams and gels including estrogen and/or testosterone, antidepressants (e.g., nortriptyline, amitriptyline), and anti-anxiety drugs; and injectable medications including anesthetics, estrogens, or systemic or local steroids. For example, cortisone and local anaesthetic can be injected where the pudendal nerve is identified in its canal; however, these are not always effective and can have undesirable side effects. Intractable cases of vulvodynia can be treated with injection or surgical destruction of the pudendal nerve; however, the procedure has several potential complications (e.g., permanent vulva numbness, continued vulvodynia pain, etc.).

In another example, vaginismus is an involuntary spasm of the muscles (e.g., a reflex of the pubococcygeus muscle) surrounding the vagina. Vaginismus is characterized by spasms that close the vagina making vaginal penetration during sex difficult, painful or impossible. In cases that are determined to be physically manifested, clinicians have treated female patients having vaginismus with onabotulinumtoxinA (sold under the trademark BOTOX) to relax the muscles around the vagina to assist in penetration. However, this is not always effective, can have undesirable side effects and the treatments have limited duration (e.g., 4 months). Pain with sexual intercourse, known as dyspareunia, can be another manifestation of excess pain signal transmission from the pelvic floor, vagina, surgical sites, and/or cervix.

Other sources of pelvic pain can be derived from nerve disorders such as plexopathy. For example, a sacral and/or lumbosacral plexopathy is a disorder affecting the sympathetic nerves of the lumbosacral plexus (e.g., the anterior divisions of the lumbar nerves, sacral nerves, and coccygeal nerve), which can be caused by trauma, nerve compression, vascular disease, metabolic disease (e.g., diabetes), or infection. Symptoms associated with a plexopathy include pain, loss of motor control and sensory deficits among others. Mild cases can be treated with short or long-term administration of analgesia and/or muscle relaxers. More severe cases can require additional treatments such as surgical decompression of the nerve plexus center or other neurovascular surgical intervention to address the pain.

II. Neuromodulation for Treatment of Pain

A. Neuromodulation of the Celiac Plexus and/or the Celiac Ganglia

The celiac plexus is a complex network of nerves located in the abdomen, where the celiac artery, superior mesenteric artery, and renal arteries branch from the abdominal aorta. The celiac plexus is located caudal to the diaphragm (in an antecrural position), surrounds the origin of the celiac trunk, and comprises a dense network of ganglia (e.g., celiac ganglia) and interconnecting fibers. The celiac plexus includes a number of smaller plexuses, such as the hepatic plexus, splenic plexus, gastric plexus, pancreatic plexus and suprarenal plexus. The celiac plexus is known to transmit pain sensation originating from the pancreas as well as most of the abdominal viscera with the exception of the colon, rectum and pelvic organs (Levy et. al. *Gastrointestinal Endoscopy Clinics of North America*. 2012; 22: 231-47, viii, herein incorporated by reference in its entirety). For example, the neurons that innervate the pancreas can receive nociceptive stimulation and then transmit this pain information to the celiac plexus, and then to the thalamus and cortex of the brain, thereby inducing the sensation of pain. A ganglion is defined as a collection of nerve cell bodies and glial cells that are interconnected via a sense network of neural rami and septae of connective tissue. The celiac ganglia can be detected, for example, using endoscopic ultrasound or other techniques (e.g., CT, fluoroscopy). For example, visualized ganglia are typically located adjacent to the celiac artery, anterior to the aorta, and are predominantly oval or almond-shaped, ranging in size from 2 to 20 mm.

Neuromodulation of the celiac plexus and/or the celiac ganglia is the partial or complete incapacitation or other effective disruption or regulation of nerves innervating the pancreas, e.g., nerves terminating in or originating from the pancreas or in structures closely associated with the pancreas) and/or nerves innervating the liver, gallbladder, stomach, spleen, kidney, small intestine, ascending and transverse colon and the ovarian theca, respectively. In particular, neuromodulation of the celiac plexus comprises inhibiting, reducing, blocking, pacing, up-regulating, and/or down-regulating neural communication along neural fibers (e.g., efferent and/or afferent neural fibers) innervating the pancreas, or in other embodiments, innervating the liver, gallbladder, and other abdominal organs. In other embodiments, the treatment procedure can target a subset of nerves of a smaller plexus within the celiac plexus, such as the hepatic plexus (e.g., along the hepatic artery), the splenic plexus (e.g., along the splenic artery), the gastric plexus (e.g., along the left gastric artery), and the pancreatic plexus (e.g., along the pancreatic artery). These targets can be intravenously accessed through femoral, brachial or radial approaches where a catheter could be navigated through the celiac trunk to the subsidiary arteries (e.g., hepatic, splenic, pancreatic, etc.). Such incapacitation, disruption, and/or regulation can be long-term (e.g., permanent or for periods of months, years, or decades) or short-term (e.g., for periods of minutes, hours, days, or weeks).

Sympathetic neural activity via the nerve fibers of the celiac plexus and/or celiac ganglion, and particularly sympathetic afferent nerves, are responsible for carrying pain signals from the abdominal viscera to the brain in patients e.g., patients with conditions and diseases of the pancreas, including, but not limited to, acute pancreatitis, chronic pancreatitis, and pancreatic cancer. Neuromodulation of the celiac plexus and/or the celiac ganglia is expected to be useful in reducing perceived pain associated with these conditions, as well as pain associated with hepatobiliary disease and visceral artery insufficiency. Methods and systems for neuromodulation of the celiac plexus and/or celiac ganglia for efficaciously treating and/or reducing pain associated with several clinical conditions of the abdominal viscera are described herein.

Furthermore, afferent sympathetic activity from the abdominal viscera can contribute to central sympathetic tone or drive. Accordingly, neuromodulation of the celiac plexus and/or celiac ganglia is expected to be useful in treating clinical conditions associated with central sympathetic activity (e.g., overactivity or hyperactivity), particularly conditions associated with central sympathetic overstimulation. Conditions associated with central sympathetic activity (e.g., overactivity or hyperactivity) include, for example, hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, osteoporosis, and sudden death, among other conditions. Accordingly, in some patients, reducing localized sympathetic drive via the celiac plexus and/or celiac ganglia, central sympathetic drive, and/or other benefits from neuromodulation can outweigh the complete or partial loss of pancreatic-nerve functionality. Moreover, disrupting efferent and/or afferent nerve traffic to/from the visceral abdominal organs (e.g., stomach, intestines, liver, pancreas) may conceivably impact hormonal activity in the abdominal organs and thereby impact conditions associated with overfeeding, obesity, insulin resistance, and diabetes among other conditions. Structures in the abdominal viscera may also be important in sequestration of intra and extravascular fluid, and denervation (e.g., complete or partial) of these organs could thereby also impact conditions of fluid excess (e.g., heart failure).

B. Neuromodulation of the Superior Mesenteric Plexus and/or the Superior Mesenteric Ganglion The superior mesenteric plexus is a continuation of the lower part of the celiac plexus. The superior mesenteric plexus surrounds the superior mesenteric artery and divides into a number of secondary plexuses and/or gives rise to sympathetic nerve fibers innervating the pancreas, the small intestine, and colon in the abdomen. The superior mesenteric ganglion is the synapse point for one of the pre- and post-synaptic nerves of the sympathetic division of the autonomic nervous system. Specifically, contributions to the superior mesenteric ganglion arise from TV10 and TV11, and these nerve fibers go on to innervate the small intestine, the ascending colon and the transverse colon.

Neuromodulation of the superior mesenteric plexus and/or the superior mesenteric ganglia is the partial or complete incapacitation or other effective disruption or regulation of nerves innervating the pancreas (e.g., nerves terminating in or originating from the pancreas or in structures closely associated with the pancreas) and/or nerves innervating the small intestine, and ascending and transverse colon. In particular, neuromodulation of the superior mesenteric plexus comprises inhibiting, reducing, blocking, pacing, up-regulating, and/or down-regulating neural communication along neural fibers (e.g., efferent and/or afferent neural fibers) innervating the pancreas, or in other embodiments, innervating the small intestine, and ascending and transverse colon. Such incapacitation, disruption, and/or regulation can be long term (e.g., permanent or for periods of months, years, or decades) or short-term (e.g., for periods of minutes, hours, days, or weeks).

Similar to the sympathetic neural activity via the nerve fibers of the celiac plexus and/or celiac ganglion, the sympathetic neural activity associated with the superior mesenteric plexus and/or the superior mesenteric ganglia can be associated with carrying pain signals from the abdominal viscera to the brain in patients e.g., patients with conditions and diseases of the pancreas, including, but not limited to, acute pancreatitis, chronic pancreatitis, and pancreatic cancer. Neuromodulation of the superior mesenteric plexus and/or the superior mesenteric ganglia is expected to be useful in reducing perceived pain associated with these conditions, as well as pain associated with pain causing conditions (e.g., cancer) associated with the small intestine and colon and with visceral artery insufficiency. Also as described above, neuromodulation of the superior mesenteric plexus and/or the superior mesenteric ganglia is also expected to be useful in treating clinical conditions associated with central sympathetic activity (e.g., overactivity or hyperactivity), particularly conditions associated with central sympathetic overstimulation. Methods and systems for neuromodulation of the superior mesenteric plexus and/or the superior mesenteric ganglia for efficaciously treating and/or reducing pain associated with several clinical conditions of the abdominal viscera, are further described herein.

C. Neuromodulation of Sympathetic Nerve Fibers Innervating Reproductive Organs and the Pelvic Region 1. Sympathetic Nerves Innervating the Testes and Penile Tissue The spermatic plexus is derived from the renal plexus, and it accompanies the testicular artery (e.g., internal spermatic artery) to innervate the testis. Testicular and/or penile sympathetic nerves (e.g., sympathetic nerves along the testicular vessels, pudendal vessels or other associated structures), innervate portions of the male genitalia. For example, the genitofemoral nerve, which originates from the upper part of the lumbar plexus, is responsible for both the efferent and afferent (along with the ilioinguinal nerve) limbs of the cremasteric reflex where it innervates the cremaster muscle and the scrotal skin. The ilioinguinal nerve accompanies the spermatic cord and supplies the scrotal skin, skin over the root of the penis, groin and medial thigh. The pudendal nerve originates in the sacral plexus and accompanies the internal pudendal vessels and eventually gives rise to the perineal nerve and the dorsal nerve of the penis in males. The perineal nerve which sits adjacent and below the internal pudendal artery and becomes the posterior scrotal nerves in males. The neurons that innervate the testes, scrotum and penis can receive nociceptive stimulation and then transmit this pain information to the spermatic plexus, the lumbar plexus, the sacral plexus, etc. and then to the thalamus and cortex of the brain, thereby inducing the sensation of pain. To reduce perceived chronic pain associated with conditions or diseases associated with the testes (e.g., orchialgia) and/or penis (e.g., injury, Peyronie's disease), at least partial neuromodulation of these nerve fibers can be performed.

2. Sympathetic Nerves Innervating the Vulva, Vagina and/or Clitoris and Other Female Reproductive Structures Sympathetic nerves derived from the lumbar plexus, the sacral plexus, the uterovaginal plexus and/or particular sympathetic nerves innervating the vulva, vagina, and/or clitoris (e.g., perineal nerve, ilioinguinal nerve, genitofemoral nerve, pudendal nerve), can transmit pain signals associated with female reproductive organ or genitalia dysfunction to the brain. For example, the genitofemoral nerve, which originates from the upper part of the lumbar plexus, is responsible for both efferent and afferent (along with the ilioinguinal nerve) nerve fibers to the skin covering the mons pubis and the labium majus (e.g., anterior portion of the vulva which includes the labia majora, and surrounds the structures of the vulval vestibule such as the labia minora, clitoris and vaginal opening) in females. The pudendal nerve, which originates in the sacral plexus, gives rise to the perineal nerve and the dorsal nerve of the clitoris in females. For example, the perineal nerve which is adjacent to and below the internal pudendal artery gives rise to the posterior labial nerves in females. The vaginal plexus arises from the lower part of the pelvic plexus (e.g., the inferior hypogastric plexus) which is a plexus of nerves that supplies the viscera of the pelvic cavity and accompany the branches of the internal iliac artery (e.g., vaginal arteries, vaginal venous plexus). The vaginal plexus is distributed to the walls of the vagina to the erectile tissue of the vestibule and to the clitoris. The uterine plexus accompanies the uterine artery to the side of the uterus between the layers of the broad ligament and it communicates with the ovarian plexus. Accordingly, to reduce perceived chronic pain associated with conditions or diseases associated with the lumbar plexus, the sacral plexus, the uterovaginal plexus and/or particular sympathetic nerves innervating the vulva, vagina, and/or clitoris, at least partial neuromodulation of these nerve fibers can be performed.

3. Other Sympathetic Nerves Innervating the Pelvic Region

Often, the sacral plexus and the lumbar plexus are considered to be one large nerve plexus, the lumbosacral plexus. In front of the sacral plexus are the internal iliac artery, internal iliac vein, the ureter, and the sigmoid colon. The superior gluteal artery and vein run between the lumbosacral trunk (e.g., wherein the sacral and lumbar plexuses join) and the first sacral nerve, and the inferior gluteal artery and vein run between the second and third sacral nerves. Nociceptive stimulation from the pelvic region, such as due to trauma, nerve compression, vascular disease, infection, or otherwise diagnosed as a sacral plexopathy, can be transmitted through the lumbosacral plexus to the brain. To reduce perceived chronic pain associated with conditions or diseases associated with sacral plexopathy, at least partial neuromodulation of these nerve fibers can be performed.

4. Aspects of Neuromodulation Sympathetic Nerve Fibers Innervating Reproductive Organs and the Pelvic Region To address any one of the above conditions or diseases, neuromodulation of the appropriate sympathetic nerves can be performed. For example, the spermatic plexus, the genital branch of the genitofemoral nerve, the ilioinguinal nerve, the sacral plexus, the pudendal nerve, the perineal nerve, the vaginal plexus, the uterine plexus and/or the lumbosacral plexus can include the partial or complete incapacitation or other effective disruption or regulation of nerves innervating the testes, penis, vulva, vagina, clitoris, uterus, and/or other structures associated with the pelvic region. In particular, neuromodulation of these nerve structures comprises inhibiting, reducing, blocking, pacing, up-regulating, and/or down-regulating neural communication along neural fibers (e.g., efferent and/or afferent neural fibers) innervating the male reproductive organs (e.g., the testes, penis) or, in other embodiments, innervating the female reproductive organs (e.g., the vulva, vagina, clitoris, uterus, and ovaries) for the treatment of pain. These targets can be intravenously accessed through femoral, brachial or radial approaches where a catheter could be navigated through the femoral and iliac vessels (and its branches), and in some approaches through the aorta to the subsidiary arteries (e.g., testicular vessels, etc.). Such incapacitation, disruption, and/or regulation can be long-term (e.g., permanent or for periods of months, years, or decades) or short-term (e.g., for periods of minutes, hours, days, or weeks). While long-term disruption of sympathetic nerve fibers innervating the reproductive organs can be desirable for alleviating chronic or incalculable pairs over longer periods of time, short-term modulation of one or more of these nerve structures may also be desirable. For example, some patients suffering from vaginismus may benefit from short-term modulation to provide alleviation of pain and/or muscle spasms of the vagina to address issues relating psychological fears associated with vaginal penetration.

Sympathetic neural activity via the nerve fibers innervating the reproductive organs, and particularly sympathetic afferent nerves, are responsible for carrying pain signals from the reproductive viscera and/or other structures in the pelvic region to the brain in patients e.g., patients with conditions and diseases of the reproductive organs and genitalia, including, but not limited to, orchialgia, injury, Peyronie's disease, vulvodynia, dyspareunia, and vaginismus. Neuromodulation of the appropriate nerve structures are expected to be useful in reducing perceived pain associated with these conditions, as well as pain associated with plexopathy in the pelvic region. Methods and systems for neuromodulation of these nerve structures for efficaciously treating and/or reducing pain associated with several clinical conditions of the reproductive viscera and genitalia, are described herein.

III. Selected Examples of Neuromodulation Modalities

Various techniques can be used to partially or completely incapacitate neural pathways, such as those innervating the pancreas, the liver, the gallbladder or other abdominal organs. Such various techniques can also be used to partially or completely incapacitate neural pathways such as those innervating the testes, penis, vulva, vagina, clitoris or other reproductive organs. Neuromodulation in accordance with embodiments of the present technology can be electrically-induced, thermally-induced, chemically-induced, or induced in another suitable manner or combination of manners at one or more suitable treatment locations during a treatment procedure. For example, the purposeful application of radiofrequency (RF) energy (monopolar and/or bipolar), pulsed RF energy, microwave energy, optical energy, ultrasound energy (e.g., intravascularly delivered ultrasound, extracorporeal ultrasound, high-intensity focused ultrasound (HIFU)), cryotherapeutic energy, direct heat energy, chemicals (e.g., drugs or other agents), radiation (e.g., infrared, visible, gamma), or combinations thereof to tissue at a treatment location can induce one or more desired effects at the treatment location, e.g., broadly across the treatment location or at localized regions of the treatment location.

Figure 2B:
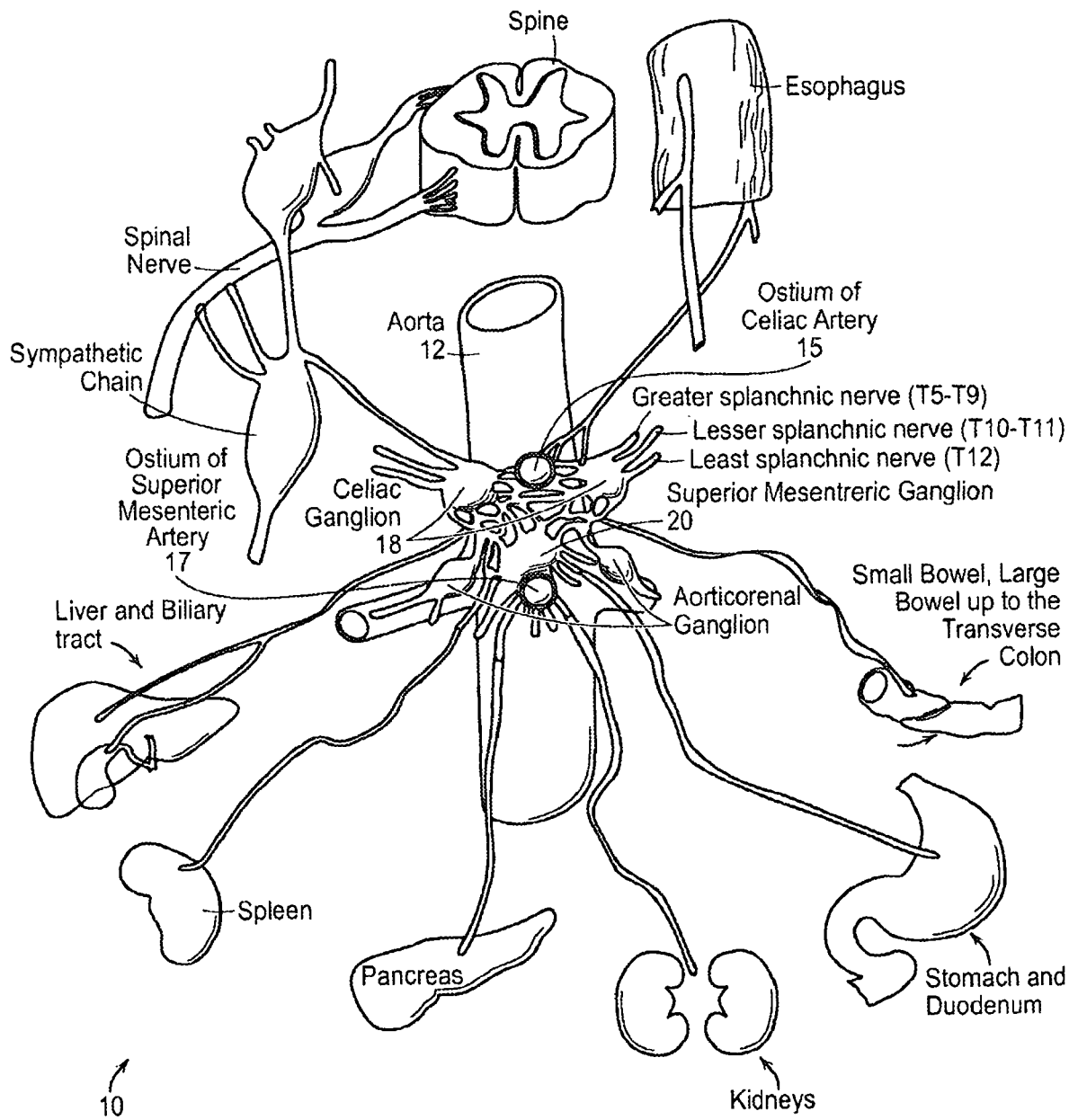

FIGS. 2A and 2B are anatomical views illustrating the abdominal viscera 10 and the major arterial vessels including, for example, the aorta 12, the celiac artery 14 and the superior mesenteric artery 16. FIGS. 2A and 2B also illustrate the sympathetic nerve structures that innervate the abdominal viscera 10, including the celiac plexus and/or celiac ganglion 18, and the superior mesenteric plexus and/or ganglion 20. Treatment procedures for neuromodulation in accordance with embodiments of the present technology can include applying a treatment modality at one or more treatment locations proximate a structure having a relatively high concentration of sympathetic nerves innervating a diseased or otherwise abnormal or targeted organ.

In some embodiments, for example, at least one treatment location can be proximate a portion of the celiac artery 14, a branch of the celiac artery 14, an ostium of the celiac artery 15, and/or another suitable structure (e.g., another suitable structure in close association the celiac plexus and/or celiac ganglion 18) in the vicinity of celiac sympathetic nerves. In other embodiments, at least one treatment location can be proximate a portion of the superior mesenteric artery 16, a branch of the superior mesenteric artery 16, an ostium of the superior mesenteric artery 17, a superior mesenteric vein (not shown), and/or another suitable structure (e.g., another suitable structure in close association the superior mesenteric ganglion 18) in the vicinity of superior mesenteric sympathetic nerves.

Figure 2C:
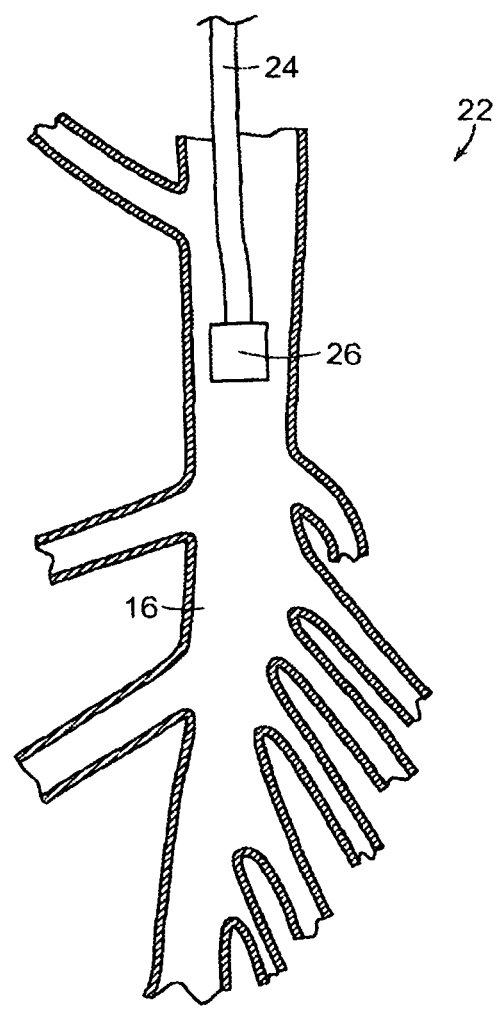
FIG. 2C is a partially cross-sectional view illustrating neuromodulation at a treatment location within the superior mesenteric artery in accordance with an embodiment of the present technology.

FIG. 2C, for example, is a cross-sectional view illustrating neuromodulation at a treatment location within the superior mesenteric artery 16. As shown in FIG. 2C, a treatment device 22 including a shaft 24 and a therapeutic element 26 can be extended toward the superior mesenteric artery 16 to locate the therapeutic element 26 at the treatment location within the superior mesenteric artery 16. The therapeutic element 26 can be configured for neuromodulation at the treatment location via a suitable treatment modality, e.g., cryotherapeutic, direct heat, electrode-based, transducer-based, chemical-based, or another suitable treatment modality. Likewise, the treatment device 22 can be located at a treatment location within the celiac artery 14 for administering neuromodulation. In other embodiments, administering neuromodulation can include administering a suitable treatment modality at more than one site, e.g., the celiac artery 14 and the superior mesenteric artery 16, for example for modulating the sympathetic nerves innervating the pancreas or another abdominal organ.

Figure 3A:
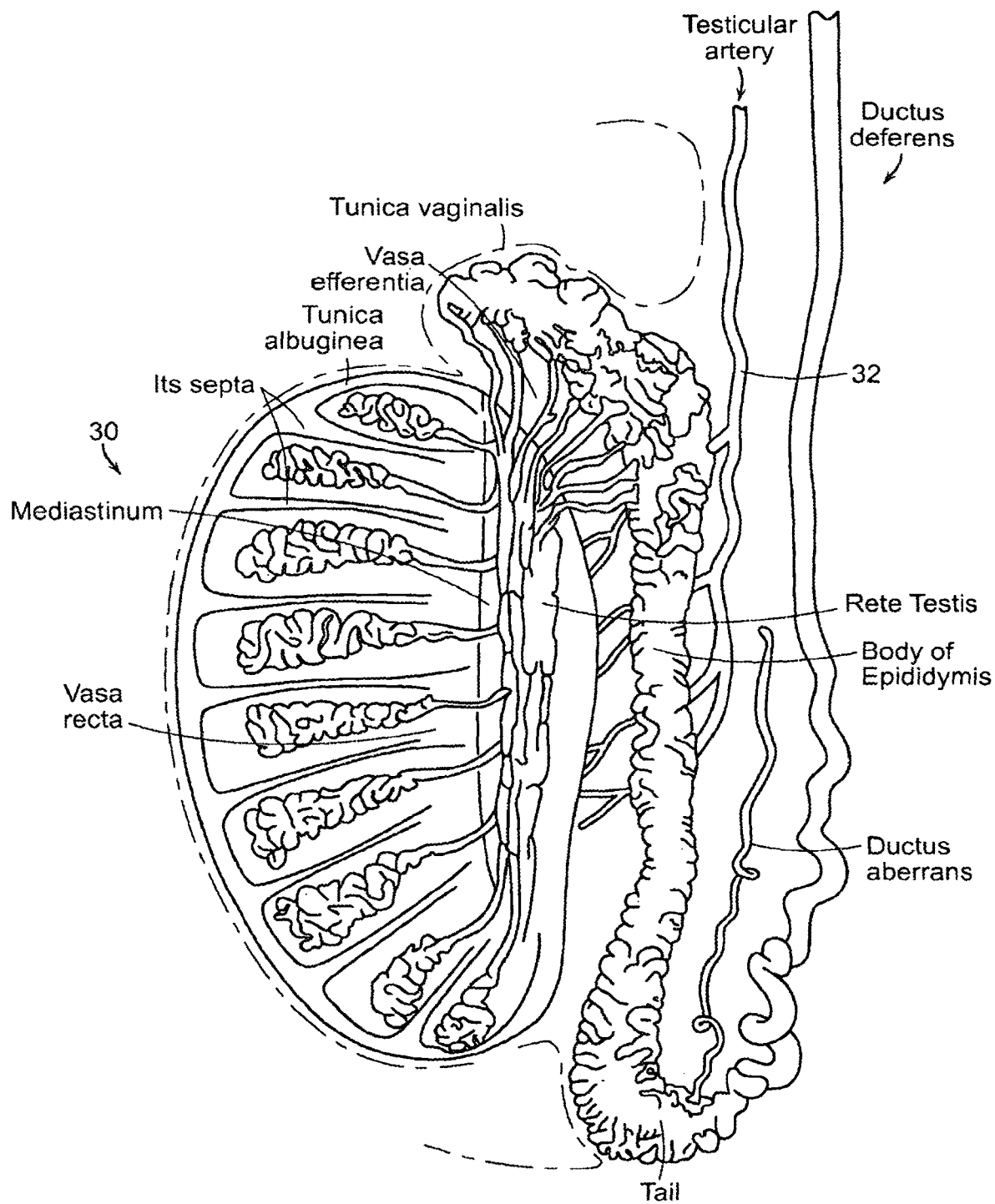
FIG. 3A is anatomical views illustrating the testicular artery and nearby organ structures and vessels.
Figure 3B:
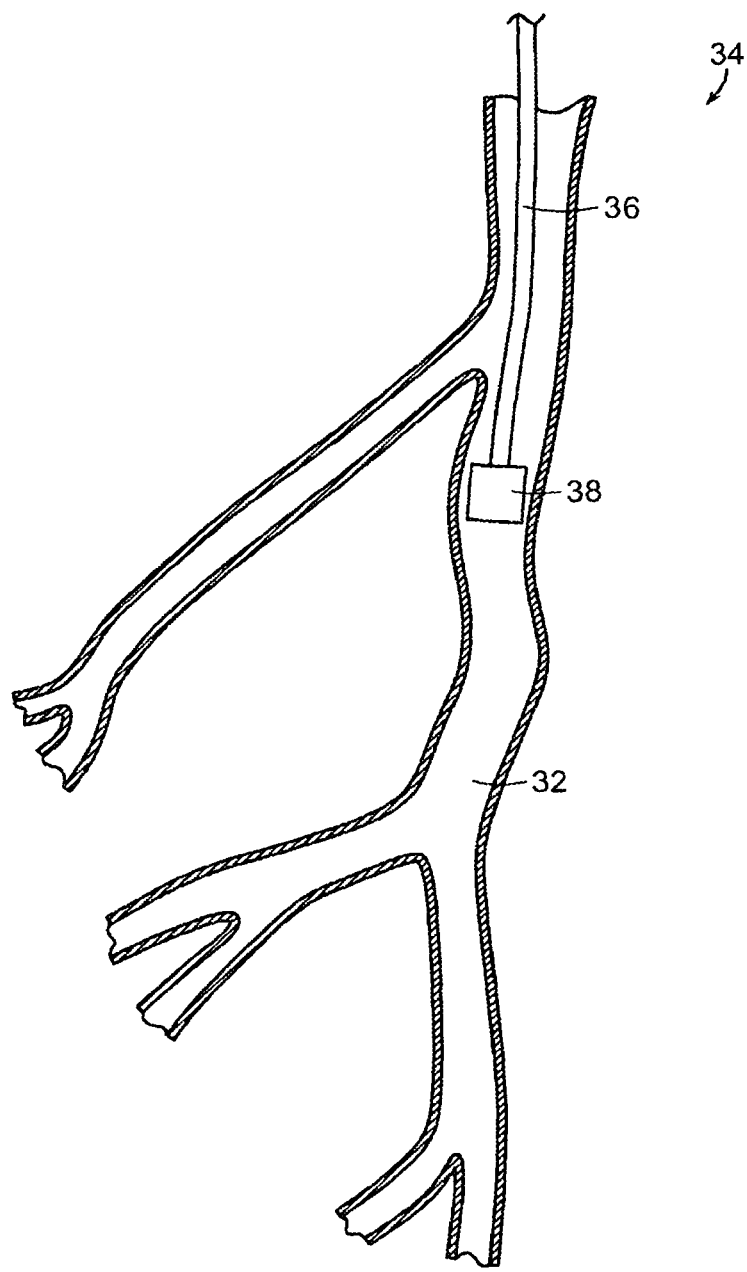
FIG. 3B is a partially cross-sectional view illustrating neuromodulation at a treatment location within the testicular artery in accordance with an embodiment of the present technology.

FIG. 3A is a cross-sectional anatomical view illustrating a testicle 30, a testicular artery 32, and nearby structures and vessels. Treatment procedures for testicular neuromodulation for the treatment of pain, for example, can include applying a treatment modality at one or more treatment locations proximate a structure having a relatively high concentration of sympathetic nerves innervating the testes. In some embodiments, for example, at least one treatment location can be proximate a portion of the testicular artery 32, a branch of the testicular artery 32, an ostium of the testicular artery 32, a testicular vein, a branch of a testicular vein, an ostium of a testicular vein, and/or another suitable structure in the vicinity of testicular nerves (e.g., nerves originating at the spermatic plexus, the genital branch of the genitofemoral nerve). FIG. 3B, for example, is a cross-sectional view illustrating neuromodulation at a treatment location within the testicular artery 32. As shown in FIG. 3B, a treatment device 34 including a shaft 36 and a therapeutic element 38 can be extended toward the testicular artery 32 to locate the therapeutic element 38 at the treatment location within the testicular artery 32. The therapeutic element 38 can be configured for neuromodulation at the treatment location via a suitable treatment modality, e.g., cryotherapeutic, direct heat, electrode-based, transducer-based, chemical-based, or another suitable treatment modality. The treatment device 34 may have a number of features generally similar to the treatment device 22 described above with reference to FIG. 2C. Further examples of suitable treatment devices are described below with reference to FIG. 7.

Figure 4:
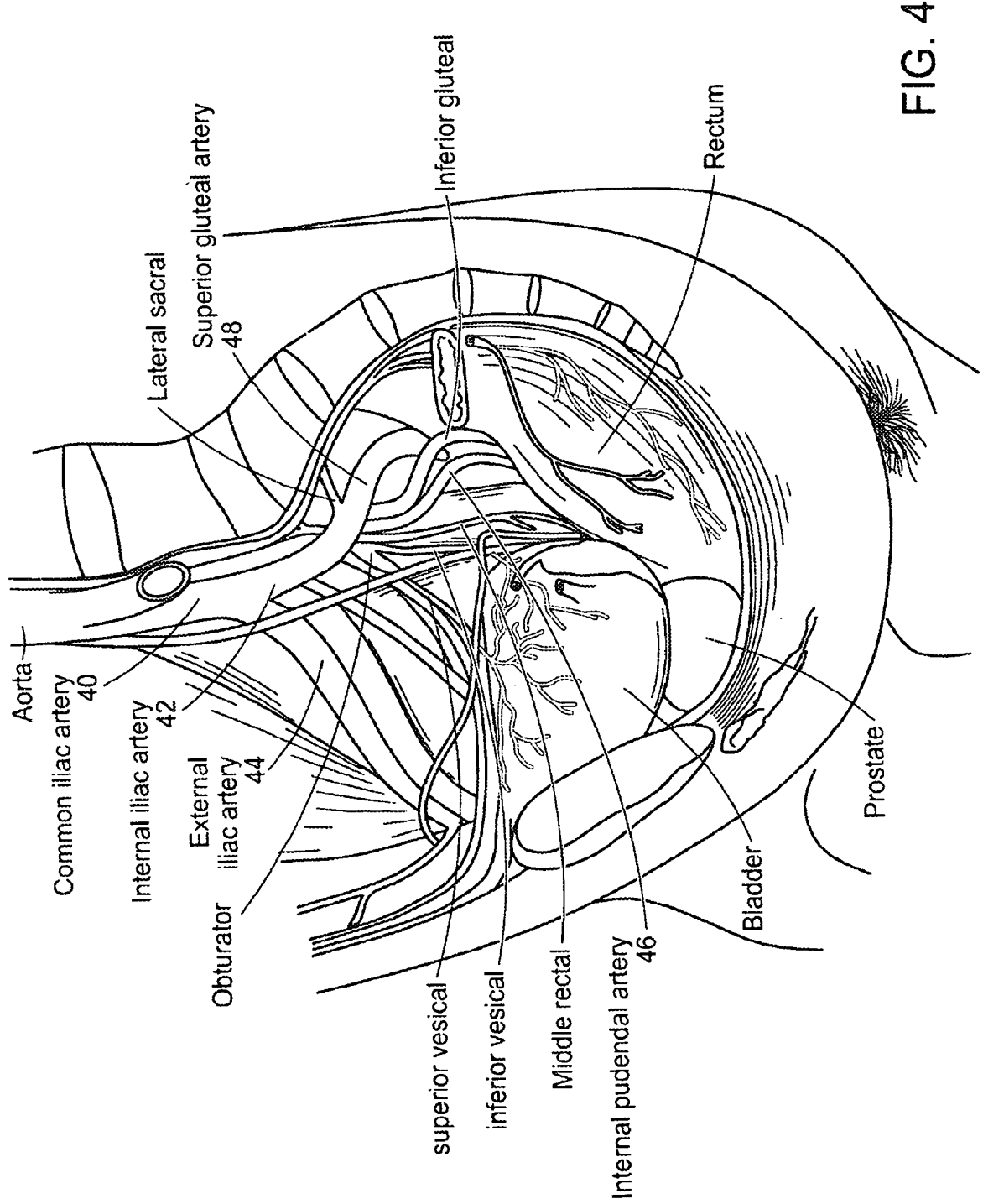
FIG. 4 is a cross-sectional anatomical view illustrating a common iliac artery, an internal iliac artery, an external iliac artery, an internal pudendal artery, a superior gluteal artery and other nearby structures and vessels.

FIG. 4 is a cross-sectional anatomical view illustrating a common iliac artery 40, an internal iliac artery 42, an external iliac artery 44, an internal pudendal artery 46, a superior gluteal artery 48 and other nearby structures and vessels. Treatment procedures for neuromodulation of the male (testes, penis) or female (e.g., vulva, vagina, clitoris) reproductive organs for the treatment of pain can include, for example, applying a treatment modality at one or more treatment locations proximate a structure having a relatively high concentration of sympathetic nerves innervating these reproductive or genital structures. In some embodiments, for example, at least one treatment location can be proximate a portion/branch/ostium of the internal iliac artery 42 (or vein) for neuromodulation of a sacral plexus, a portion/branch/ostium of the external iliac artery 44 (or vein) for neuromodulation of a genital branch of a genitofemoral nerve, a portion/branch/ostium of the internal pudendal artery 46 (or vein) for neuromodulation of a pudendal nerve or perineal nerve, a portion/branch/ostium of the superior gluteal artery 48 (or vein) for neuromodulation of a lumbosacral plexus, a portion/branch/ostium of the deep circumflex iliac artery (or vein) which is a branch of the external iliac artery 44 for neuromodulation of a ilioinguinal nerve, and/or another suitable structure in the vicinity of nerves innervating the male or female reproductive organs.

Figure 5:
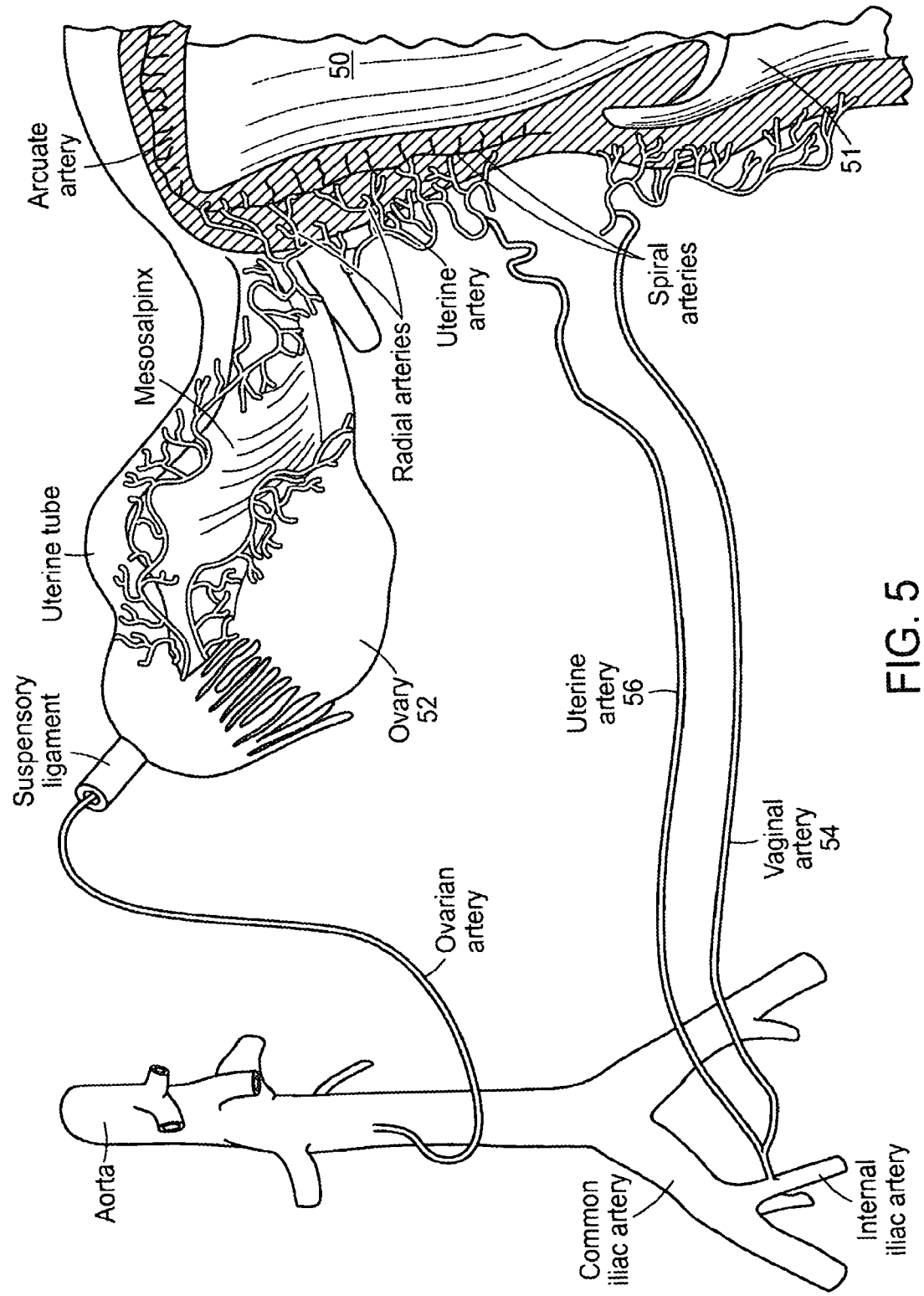
FIG. 5 is an anatomical view illustrating a portion of the uterus, vagina, an ovary and nearby organs and vessels.

FIG. 5 is an anatomical view illustrating a portion of the uterus 50, vagina 51, an ovary 52 and nearby organs and vessels, including a vaginal artery 54 and a uterine artery 56. Treatment procedures for vaginal or uterine neuromodulation in accordance with embodiments of the present technology can include applying a treatment modality at one or more treatment locations proximate a structure having a relatively high concentration of vaginal or uterine nerves, respectively. In some embodiments, for example, at least one treatment location can be proximate a portion/branch/ostium of the vaginal artery 54 (or vein) for neuromodulation of a vaginal plexus or other vaginal nerve, a portion/branch/ostium of the uterine artery 56 (or vein) for neuromodulation of a uterine plexus or other uterine nerve, and/or another suitable structure in the vicinity of sympathetic nerves innervating the uterus and/or vagina.

The treatment location can be proximate (e.g., at or near) a vessel or chamber wall (e.g., a wall of a "target vessel" such as a celiac artery, superior mesenteric artery or vein, a testicular artery or vein, a common iliac artery or vein, an internal iliac artery or vein, an external iliac artery or vein, an internal pudendal artery or vein, a superior gluteal artery or vein, deep circumflex iliac artery or vein, a vaginal artery or vein, a uterine artery or vein and/or another suitable structure for the management or treatment of pain associated with the abdominal or reproductive viscera), and the treated tissue can include tissue proximate the treatment location. For example, with regard to a celiac artery, a treatment procedure can include modulating nerves in the celiac plexus, which lay at least partially within or adjacent to the adventitia of the celiac artery. In some embodiments it may be desirable to modulate celiac nerves from a treatment location within a vessel and in close proximity to a diseased or damaged abdominal organ (e.g., pancreas), for example, closer to the diseased or damaged organ than to a trunk of the vessel. This can increase the likelihood of modulating nerves specific to the organ or viscera, while decreasing the likelihood of modulating nerves that extend to other organs. Vessels can decrease in diameter and become more tortuous as they extend toward an organ (e.g., a diseased, damaged or otherwise target organ). Accordingly, modulating nerves from a treatment location in close proximity to the target organ can include using a device (e.g., treatment devices 22, 34) having size, flexibility, and/or other characteristics suitable for accessing narrow and/or tortuous portions of vessels.

In some embodiments, the purposeful application of energy (e.g., electrical energy, thermal energy, etc.) to tissue can induce one or more desired thermal heating and/or cooling effects on localized regions of the target vessels, for example, and adjacent regions along all or a portion of the targeted sympathetic nerve fibers, which lay intimately within or adjacent to the adventitia of the target vessels. Some embodiments of the present technology, for example, include cryotherapeutic neuromodulation, which can include cooling tissue at a target site in a manner that modulates neural function. The mechanisms of cryotherapeutic tissue damage include, for example, direct cell injury (e.g., necrosis), vascular injury (e.g., starving the cell from nutrients by damaging supplying blood vessels), and sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Several embodiments of the present technology include cooling a structure at or near an inner surface of a vessel or chamber wall such that proximate (e.g., adjacent) tissue is effectively cooled to a depth where sympathetic (efferent and/or afferent) nerves reside. For example, a cooling structure can be cooled to the extent that it causes therapeutically-effective, cryogenic nerve modulation. Sufficiently cooling at least a portion of a sympathetic nerve may slow or potentially block conduction of neural pain signals from a damaged or diseased organ to the brain and/or to produce a prolonged or permanent reduction in organ sympathetic activity. In some embodiments, a cryotherapeutic treatment modality can include cooling that is not configured to cause neuromodulation. For example, the cooling can be at or above cryogenic temperatures and can be used to control neuromodulation via another treatment modality, e.g., to reduce damage to non-targeted tissue when targeted tissue adjacent to the non-targeted tissue is heated.

Cryotherapeutic treatment can be beneficial in certain embodiments. For example, rapidly cooling tissue can provide an analgesic effect such that cryotherapeutic treatment can be less painful than other treatment modalities. Neuromodulation using cryotherapeutic treatment can therefore require less analgesic medication to maintain patient comfort during a treatment procedure compared to neuromodulation using other treatment modalities. Additionally, reducing pain can reduce patient movement and thereby increase operator success and/or reduce procedural complications. Cryogenic cooling also typically does not cause significant collagen tightening, and therefore is not typically associated with vessel stenosis. In some embodiments, cryotherapeutic treatment can include cooling at temperatures that can cause therapeutic elements to adhere to moist tissue. This can be beneficial because it can promote stable, consistent, and continued contact during treatment. The typical conditions of treatment can make this an attractive feature because, for example, patients can move during treatment, catheters associated with therapeutic elements can move, and/or respiration can cause the internal organ structures to rise and fall and thereby move the associated vasculature. In addition, blood flow is pulsatile and can cause structures associated with the target organs to pulse. Cryogenic adhesion also can facilitate intravascular positioning, particularly in relatively small structures (e.g., relatively short arteries) in which stable intravascular positioning can be difficult to achieve.

As an alternative to or in conjunction with cryotherapeutic cooling, other suitable energy delivery techniques, such as electrode-based or transducer-based approaches, can be used for therapeutically-effective neuromodulation. Electrode-based or transducer-based treatment can include delivering electrical energy and/or another form of energy to tissue and/or heating tissue at a treatment location in a manner that modulates neural function. For example, sufficiently stimulating and/or heating at least a portion of a sympathetic nerve can slow or potentially block conduction of neural pain signals from a damaged or diseased organ to the brain and/or to produce a prolonged or permanent reduction in sympathetic activity. As noted previously, suitable energy modalities can include, for example, RF energy (monopolar and/or bipolar), pulsed RF energy, microwave energy, ultrasound energy (e.g., intravascularly delivered ultrasound, extracorporeal ultrasound, HIFU), extracorporeal ultrasound energy, laser energy, optical energy, magnetic, direct heat, or other suitable energy modalities alone or in combination. Where a system uses a monopolar configuration, a return electrode or ground patch fixed externally on the subject can be used. Moreover, electrodes (or other energy delivery elements) can be used alone or with other electrodes in a multi-electrode array. Examples of suitable multi-electrode devices are, described in U.S. patent application Ser. No. 13/281,360, filed Oct. 25, 2011, and incorporated herein by reference in its entirety. Other suitable devices and technologies, such as cryotherapeutic devices, are described in U.S. patent application Ser. No. 13/279,330, filed Oct. 23, 2011, and additional thermal devices are described in U.S. patent application Ser. No. 13/279,205, filed Oct. 21, 2011, each of which are incorporated herein by reference in their entireties.

Thermal effects can include both thermal ablation and non-ablative thermal alteration or damage (e.g., via sustained heating and/or resistive heating) to partially or completely disrupt the ability of a nerve to transmit a signal. Desired thermal heating effects, for example, may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for ablative thermal alteration. More specifically, exposure to thermal energy in excess of a body temperature of about 37° C., but below a temperature of about 45° C., may induce thermal alteration via moderate heating of target neural fibers or of vascular structures that perfuse the target fibers. In cases where vascular structures are affected, the target neural fibers may be denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures that perfuse the target fibers. In some patients, it may be desirable to achieve temperatures that thermally ablate the target neural fibers or the vascular structures, but that are less than about 90° C., or less than about 85° C., or less than about 80° C., and/or less than about 75° C. Other embodiments can include heating tissue to a variety of other suitable temperatures.

In some embodiments, neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. For example, the chemical can be guanethidine, ethanol, phenol, vincristine, a neurotoxin, or another suitable agent selected to alter, damage, or disrupt nerves. In some embodiments, energy (e.g., light, ultrasound, or another suitable type of energy) can be used to activate the chemical and/or to cause the chemical to become more bioavailable. A variety of suitable techniques can be used to deliver chemicals to tissue at a treatment location. For example, chemicals can be delivered via one or more devices, such as needles originating outside the body or within the vasculature or delivery pumps (see, e.g., U.S. Pat. No. 6,978,174, the disclosure of which is hereby incorporated by reference in its entirety). In an intravascular example, a catheter can be used to intravascularly position a therapeutic element including a plurality of needles (e.g., micro-needles) that can be retracted or otherwise blocked prior to deployment. In other embodiments, a chemical can be introduced into tissue at a treatment location via simple diffusion through a vessel wall, electrophoresis, or another suitable mechanism. Similar techniques can be used to introduce chemicals that are not configured to cause neuromodulation, but rather to facilitate neuromodulation via another treatment modality. Examples of such chemicals include, but are not limited to, anesthetic agents and contrast agents.

In some embodiments, a treatment procedure can include applying a suitable treatment modality at a treatment location in a testing step followed by a treatment step. The testing step, for example, can include applying the treatment modality at a lower intensity and/or for a shorter duration than during the treatment step. This can allow an operator to determine (e.g., by neural activity sensors and/or patient feedback) whether nerves proximate the treatment location are suitable for modulation. Performing a testing step can be particularly useful for treatment procedures in which targeted nerves are closely associated with nerves that could cause undesirable side effects if modulated during a subsequent treatment step.

IV. Achieving Intravascular Access to the Target Vessels

Figures 6A, 6B:
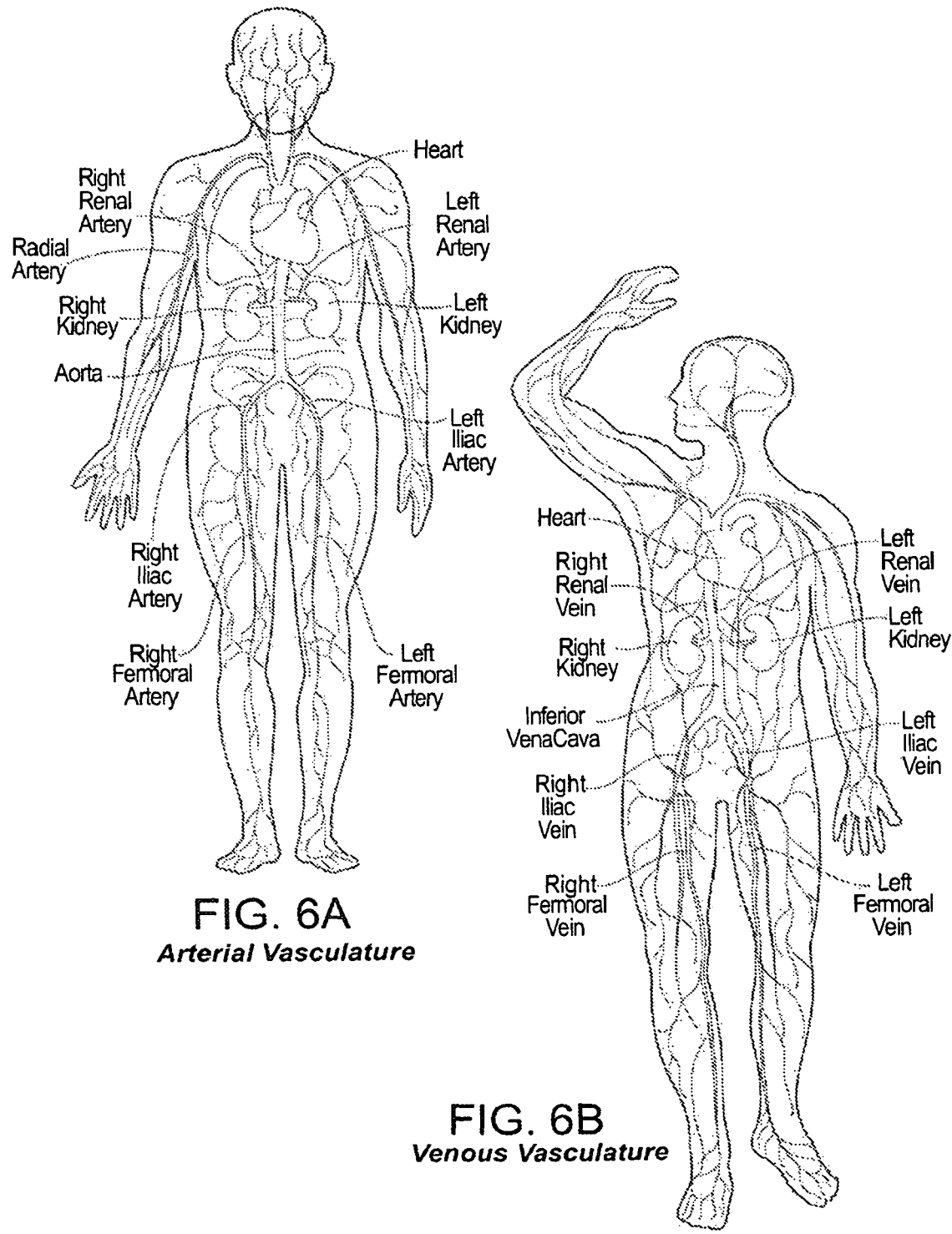
FIGS. 6A and 6B are anatomic views of the arterial vasculature and venous vasculature, respectively, of a human.

In accordance with the present technology, neuromodulation of a left and/or right celiac plexus and/or celiac ganglion 18 (FIG. 2A), which is intimately associated with a celiac artery 14 (FIG. 2A), may be achieved through intravascular access. Further, neuromodulation of a superior mesenteric ganglion 20 (FIG. 2A), which is intimately associated with a superior mesenteric artery 16 (FIG. 2A), may also be achieved through intravascular access. As FIG. 6A shows, blood moved by contractions of the heart is conveyed from the left ventricle of the heart by the aorta. The aorta descends through the thorax and bifurcates at the left and right iliac arteries. The left and right iliac arteries descend, respectively, through the left and right legs and join the left and right femoral arteries.

As FIG. 6B shows, the blood collects in veins and returns to the heart, through the femoral veins into the iliac veins and into the inferior vena cava. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter (not shown) may be inserted percutaneously into the femoral artery through this access site, passed through the iliac artery and aorta, and placed into either the celiac artery 14 or the superior mesenteric artery 16 (FIG. 2A) for the management and/or treatment of pain associated with the abdominal viscera 10 (FIGS. 2A-2B). This route comprises an intravascular path that offers minimally invasive access to a respective celiac artery 14, superior mesenteric artery 16 and/or other blood vessels (e.g., superior mesenteric vein, not shown). Alternatively, the wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the celiac and/or superior mesenteric arteries using standard angiographic technique.

In accordance with another embodiment of the present technology, neuromodulation of a left and/or right spermatic plexus, which is intimately associated with a left and/or right testicular artery 32 (FIG. 3A), may be achieved through intravascular access. Referring back to FIGS. 6A and 6B, a catheter may be inserted percutaneously into the femoral artery through this access site, passed through the iliac artery and aorta, and placed into either the left or right testicular artery 32 (FIG. 3A) for the management and/or treatment of pain associated with the testes 30 (FIGS. 3A and 3B). For the management and/or treatment of pain associated with the testes and penis in males or the vulva and clitoris in females, neuromodulation of a genital branch of genitofemoral nerve; which is intimately associated with an external iliac artery 44 (FIG. 4), may also be achieved through intravascular access by percutaneously inserting a catheter into either the left or right femoral artery (FIG. 6A), into the respective left or right common iliac artery 40 (FIGS. 4 and 6A) and down into the external iliac artery 44 (FIG. 4). Further, neuromodulation of the ilioinguinal nerve may also be achieved by accessing the deep circumflex iliac artery off of the external iliac artery 44 (FIG. 4). Additional targets for the management/treatment of pain associated with male and female genitalia/reproductive organs include the sacral plexus, which is intimately associated with a left and/or right internal iliac artery 42 (FIG. 4) or vein, and the pudendal and perineal nerves, both of which are intimately associated with left and/or right internal pudendal arteries 46 (FIG. 4) and veins. Percutaneous intravascular access to these nerve structures can include passing a catheter through the left or right femoral artery (FIG. 6A), into the respective left or right common iliac artery 40 (FIGS. 4 and 6A) and down into the internal iliac artery 44 (FIG. 4) and into the internal pudendal artery 46 (FIG. 4), if desired.

In accordance with a further embodiment of the present technology, neuromodulation of a left or right vaginal plexus, which is intimately associated with a left or right vaginal artery 54 (FIG. 5), and neuromodulation of a left or right uterine plexus, which is intimately associated with a left or right uterine artery 56 (FIG. 5) may be achieved through intravascular access. Referring to FIGS. 5, 6A, and 6B together, a catheter (not shown) may be inserted percutaneously into the left or right femoral artery through this access site, passed through the left or right iliac artery and the internal iliac artery, respectively, and placed into either the left or right vaginal artery 54 or uterine artery 56 (FIG. 5) for the management and/or treatment of pain associated with the vagina 51 or uterus 50, respectively (FIG. 5).

V. Properties and Characteristics of the Abdominal and Reproductive Organ Vasculature Properties and characteristics of the abdominal and reproductive organ vasculature impose challenges to both access and treatment methods, and to system/device designs. Since neuromodulation of the various sympathetic nerve structures innervating the abdominal viscera (e.g., celiac plexus, superior mesenteric plexus) or the reproductive viscera (e.g., spermatic plexus, vaginal plexus, uterine plexus, genitofemoral nerve, ilioinguinal nerve, pudendal nerve perineal nerve, etc.) may be achieved in accordance with embodiments of the present technology through intravascular access, various aspects of the design of apparatus, systems, and methods for achieving such neuromodulation are disclosed herein. Aspects of the technology disclosed herein address additional challenges associated with variation of, physiological conditions and architecture across the patient population and/or within a specific patient across time, as well as in response to disease states, such as pancreatitis or pancreatic cancer. For example, the design of the intravascular device and treatment protocols can address not only material/mechanical, spatial, fluid dynamic/hemodynamic and/or thermodynamic properties, but also provide particular algorithms and feedback protocols for delivering energy and obtaining real-time confirmatory results of successfully delivering energy to an intended target location in a patient-specific manner.

As discussed previously, a catheter may be advanced percutaneously into either the desired vasculature targets via a minimally invasive intravascular path. However, minimally invasive arterial or venous access may be challenging, for example, because as compared to some other larger arteries that are routinely accessed using catheters, some of the target arteries (e.g., testicular arteries, internal iliac artery, etc.) can be tortuous, may be of relatively small diameter, and/or may require adjustments to the length and flexibility of the catheters. Arterial anatomy also may vary significantly from patient to patient, which further complicates minimally invasive access. Significant inter-patient variation may be seen, for example, in relative tortuosity, diameter, and/or length. Apparatus, systems and methods for achieving neuromodulation via intravascular access can account for these and other aspects of arterial anatomy and its variation across the patient population when minimally invasively accessing an artery. For example, spiral or helical computed tomography (CT) technology can be used to produce 3D images of, the vascular features for individual patients, and intravascular path choice as well as device size/diameter, length, flexibility, torque-ability, kink resistance, etc. can be selected based upon the patient's specific vascular features.

In addition to complicating arterial access, specifics of the abdominal or reproductive anatomy also complicate establishment of stable contact between neuromodulatory apparatus and a lumina) surface or wall of an artery or vein. When the neuromodulatory apparatus includes an energy delivery element, such as an electrode, transducer, heating element or a cryotherapeutic device, consistent positioning and appropriate contact force applied by the energy or cryotherapy delivery element to the vessel wall, and adhesion between the applicator and the vessel wall can be important for predictability. However, navigation can be impeded by the tight space within an artery, as well as tortuosity of the artery. Furthermore, establishing consistent contact can be complicated by patient movement, respiration, and/or the cardiac cycle because these factors may cause significant movement of the artery relative to the aorta, for example, and the cardiac cycle may transiently distend the target artery (i.e., cause the wall of the artery to pulse). To address these challenges, the treatment device or applicator may be designed with relative sizing and flexibility considerations. For example, the artery may have an internal diameter less than approximately 1.7 mm and the treatment device can be delivered using a 3 French, or in some cases, a 4 French sized catheter. To address challenges associated with patient and/or arterial movement during treatment, the treatment device and neuromodulation system can be configured to use sensory feedback, such as impedance and temperature, to detect instability and to alert the operator to reposition the device and/or to temporarily stop treatment. In other embodiments, energy delivery algorithms can be varied in real-time to account for changes detected due to patient and/or arterial movement. In further examples, the treatment device may include one or more modifications or movement resistant enhancements such as atraumatic friction knobs or barbs on an outside surface of the device for resisting movement of the device relative to the desired tissue location, positionable balloons for inflating and holding the device in a consistent and stable position during treatment, or the device can include a cryogenic component that can temporarily freeze or adhere the device to the desired tissue location.

After accessing a desired target artery and facilitating stable contact between neuromodulatory apparatus and a luminal surface of the artery, nerves in and around the adventitia of the artery can be modulated via the neuromodulatory apparatus. Effectively applying thermal treatment from within an artery is non-trivial given the potential clinical complications associated with such treatment. For example, the intima and media of the artery are highly vulnerable to thermal injury. As discussed in greater detail below, the intima-media thickness separating the vessel lumen from its adventitia means that target nerves may be multiple millimeters distant (e.g., 1-3 mm) from the lumina) surface of the artery. Sufficient energy can be delivered to or heat removed from the target sympathetic nerve fibers to modulate the target nerves without excessively cooling or heating the vessel wall to the extent that the wall is frozen, desiccated, or otherwise potentially affected to an undesirable extent. For example, when employing energy modalities such as RF or ultrasound, energy delivery can be focused on a location further from the interior vessel wall. In one embodiment, the majority of the RF or ultrasound energy can be focused on a location (e.g., a "hot spot") 1-3 mm beyond the interior surface of the vessel wall. The energy will dissipate from the hot spot in a radially decreasing manner. Thus, the targeted nerves can be modulated without damage to the luminal surface of the vessel. A potential clinical complication associated with excessive heating is thrombus formation from coagulating blood flowing through the artery. Given that this thrombus may cause irreversible damage to the abdominal or reproductive organ, thermal treatment from within the artery can be applied carefully. Accordingly, the complex fluid mechanics and thermodynamic conditions present in the artery during treatment, particularly those that may impact heat transfer dynamics at the treatment site, may be important in applying energy (e.g., heating thermal energy) and/or removing heat from the tissue (e.g., cooling thermal conditions) from within the artery.

The neuromodulatory apparatus can also be configured to allow for adjustable positioning and repositioning of a thermal energy delivery element (e.g., electrode, transducer, heating element, cryotherapeutic element or device, etc.) within the artery since location of treatment may also impact clinical efficacy. For example, it may be tempting to apply a full circumferential treatment from within the artery given that the nerves may be spaced circumferentially around an artery. In some situations, a full-circle lesion likely resulting from a continuous circumferential treatment may be potentially related to artery stenosis. Therefore, the formation of more complex lesions along a longitudinal dimension of the artery via the cryotherapeutic devices or other energy delivery elements (e.g., electrodes, transducers, etc.) and/or repositioning of the neuromodulatory apparatus to multiple treatment locations may be desirable. It should be noted, however, that a benefit of forming a circumferential lesion or ablation may outweigh the potential of artery stenosis or the risk may be mitigated with certain embodiments or in certain patients and forming a circumferential lesion or ablation could be a goal. Additionally, variable positioning and repositioning of the neuromodulatory apparatus may prove to be useful in circumstances where the artery is particularly tortuous or where there are proximal branch vessels off the artery main vessel, making treatment in certain locations challenging.

Blood flow through an artery may be temporarily occluded for a short time with minimal or no complications. However, occlusion for a significant amount of time can be avoided in some cases to prevent injury to the organ such as ischemia. It can be beneficial to avoid occlusion altogether or, if occlusion is beneficial, to limit the duration of occlusion (e.g., 2-5 minutes).

VI. Methods for Treatment and Management of Pain

Disclosed herein are several embodiments of methods directed to treatment or management of pain associated with the abdominal and/or reproductive viscera using neuromodulation. The methods disclosed herein may represent various advantages over a number of conventional approaches and techniques in that they allow for the potential targeting of sympathetic nerve fibers (e.g., afferent nerve fibers) that transmit pain information from nociceptive receptors at a disease or damaged organ site to the cortex of the brain, thereby alleviating or reducing the sensation of pain. In some embodiments, the neuromodulation may also reduce an elevated sympathetic drive, which may contribute to multiple manifestations of disease states. Also, the disclosed methods provide for localized treatment and limited duration treatment regimens (e.g., one-time treatment), thereby reducing patient long-term treatment compliance issues, side-effects from long-term usage of pain medications, etc.

In certain embodiments, the methods provided herein comprise performing neuromodulation, thereby decreasing sympathetic nerve activity (e.g., afferent nerve activity), reducing transmission of pain information from a diseased or damaged organ site and alleviating or reducing the sensation of pain experienced by the patient. Neuromodulation may be repeated one or more times at various intervals until a desired sympathetic nerve activity level or another therapeutic benchmark is reached. In one embodiment, a decrease in sympathetic nerve activity and/or a reduction in transmission of pain signals from a diseased/damaged organ site can be evaluated by assessing a pain level and/or level of function of in the patient following the neuromodulation treatment procedure. For example, a patient can be assessed for pain level, quality, and/or level of function using one or more pain measurement scales such as the standardized Visual Analog Scale (VAS) shown in FIG. 1A both before a neuromodulation treatment and following a neuromodulation treatment. In another embodiment, for example, a decrease in sympathetic nerve activity may be observed via a marker of sympathetic nerve activity in patients experiencing pain, such as decreased levels of plasma norepinephrine (noradrenaline). Other measures or markers of sympathetic nerve activity can include muscle sympathetic nerve activity (MSNA), norepinephrine spillover, and/or heart rate variability.

In certain embodiments of the methods provided herein, neuromodulation is expected to result in a change in sympathetic nerve activity over a specific timeframe. For example, in certain of these embodiments, sympathetic nerve activity levels and/or a reported level of pain are decreased over an extended timeframe, e.g., within 1 month, 2 months, 3 months, 6 months, 9 months or 12 months post-neuromodulation. In a specific embodiment, a reported level of pain (e.g., as assessed on one or more pain measurement scales, FIGS. 1A-1E), can be decreased by about 5%, about 10%, about 15%, about 20%, about 30%, about 40%, about 50%, about 75%, or about 90%. In other embodiments, patients may report that no measurable pain is experienced following a neuromodulation procedure.

In several embodiments, the methods disclosed herein may comprise an additional step of measuring sympathetic nerve activity levels, and in certain of these embodiments, the methods can further comprise comparing the activity level to a baseline activity level. Such comparisons can be used to monitor therapeutic efficacy and to determine when and if to repeat the neuromodulation procedure. In certain embodiments, a baseline sympathetic nerve activity level is derived from the subject undergoing treatment. For example, baseline sympathetic nerve activity level may be measured in the subject at one or more timepoints prior to treatment. A baseline sympathetic nerve activity value may represent sympathetic nerve activity at a specific timepoints before neuromodulation, or it may represent an average activity level at two or more timepoints prior to neuromodulation. In certain embodiments, the baseline value is based on sympathetic nerve activity immediately prior to treatment (e.g., after the subject has already been catheterized). Alternatively, a baseline value may be derived from a standard value for sympathetic nerve activity observed across the population as a whole or across a particular subpopulation. In certain embodiments, post-neuromodulation sympathetic nerve activity levels are measured in extended timeframes post-neuromodulation, e.g., 3 months, 6 months or 12 months post-neuromodulation.

In certain embodiments of the methods provided herein, the methods are designed to decrease sympathetic nerve activity to a target level. In these embodiments, the methods include a step of measuring sympathetic nerve activity levels post-neuromodulation (e.g., 6 months post-treatment, 12 months post-treatment, etc.) and comparing the resultant activity level to a baseline activity level as discussed above. In certain of these embodiments, the treatment is repeated until the target sympathetic nerve activity level is reached. In other embodiments, the methods are simply designed to decrease sympathetic nerve activity below a baseline level without requiring a particular target activity level.

Neuromodulation may be performed on a patient having chronic debilitating or intractable pain or having one or more positive diagnosis of a condition or disease associated with chronic pain (e.g., pancreatitis, pancreatic cancer, Orchialgia, vulvodynia, etc.) to reduce one or more measurable physiological pain levels corresponding to the chronic pain. In certain embodiments of the methods provided herein, the methods are designed to decrease or reduce a patient-perceived or clinician-observed level of pain (e.g., quality, quantity, level of function, etc.) to a target level. In these embodiments, the methods include a step of measuring pain levels using, for example, one or more pain scales (FIGS. 1A-1E) before neuromodulation. In some cases, the pre-neuromodulation level of pain can be an average level of pain (e.g., averaged over days, weeks, months, years) reported by the patient or observed by a qualified observant (e.g., clinician). The methods can also include a step of measuring pain levels using at least one of the same pain scales used pre-neuromodulation to assess levels of pain post-neuromodulation (e.g., 1 month post-treatment, 3 months post-treatment, 6 months post treatment, 12 months post-treatment, etc.) and comparing the resultant pain level to the pre-neuromodulation pain level as discussed above. In certain of these embodiments, the treatment is repeated until the target pain level is reached. In other embodiments, the methods are simply designed to decrease a pain level below a desired baseline pain level without requiring a particular target pain level.

In a particular example, a patient having chronic pain associated with a disease or condition of an abdominal organ (e.g., pancreas, liver, gallbladder, etc.) can be assessed pre-neuromodulation for a level of pain intensity using the VAS. The patient's mark on the VAS line can be translated to a score from 1 to 10. The patient can undergo neuromodulation treatment targeting the celiac plexus (via the celiac artery), the superior mesenteric plexus (via the superior mesenteric artery or vein), or both. The patient can be assessed post-neuromodulation for a level of pain intensity using the VAS where the patient's mark on the VAS line can be translated to a score from 1 to 10. In one embodiment, the post-neuromodulation score is less than the pre-neuromodulation score after a determined amount of time, e.g., within 1 month, 2 months, 3 months, 6 months, 9 months or 12 months post-neuromodulation. In particular embodiments, the post-neuromodulation score is less than the pre-neuromodulation score by an amount greater than about 20%, about 30%, about 50%, about 70%, or about 90%. In addition to or instead of affecting the intensity of pain as determined by a VAS score, for example, neuromodulation may increase a patient's function level (e.g., as assessed by a functional pain scale, FIG. 1E).

In some embodiments, reduction of sympathetic activity of target nerves via neuromodulation may also reduce elevated central sympathetic drive. In some embodiments, neuromodulation of a target sympathetic nerve can be used to reduce central sympathetic drive in a patient diagnosed with a damaged or diseased organ that is associated with chronic pain. In some embodiments, for example, MSNA can be reduced by at least about 10% in the patient within about three months after at least partially inhibiting sympathetic neural activity in nerves proximate a target blood vessel innervating the damaged or diseased organ. Similarly, in some instances local norepinephrine spillover to plasma can be reduced at least about 20% in the patient within about three months after at least partially inhibiting sympathetic neural activity in nerves proximate a target blood vessel innervating the organ. Additionally, measured local norepinephrine content (e.g., assessed via biopsy, assessed in real-time via intravascular blood collection techniques, etc.) can be reduced (e.g., at least about 5%, 10%, or in another embodiment, by at least 20%) in the patient within about three months after at least partially inhibiting sympathetic neural activity in nerves proximate a target blood vessel innervating the organ.

In another prophetic example, a male patient diagnosed with orchialgia can be subjected to a baseline assessment (e.g., self-reporting) indicating a first set of measurable pain levels corresponding to the orchialgia. Such parameters can include, for example, perceived pain intensity, pain quality, and level of function/activity. Following baseline assessment, the patient can be subjected to a testicular neuromodulation procedure. Such a procedure can, for example, include any of the treatment modalities described herein or another treatment modality in accordance with the present technology. The treatment can be performed on nerves proximate one or both testes of the patient. Following the treatment (e.g., 1, 3, 6, or 12 months following the treatment), the patient can be subjected to a follow-up assessment. The follow-up assessment can indicate a measurable improvement in one or more measurable pain levels corresponding to the orchialgia.

The methods described herein address the pain information transmitted from nociceptive receptors at a disease or damaged organ site to the cortex of the brain via sympathetic nerve fibers (e.g., afferent nerve fibers). In contrast, known therapies currently prescribed for chronic pain sufferers typically address require long-term use of pain medications and other pharmaceutical agents which can have significant limitations including limited efficacy, undesirable side effects and can be subject to adverse or undesirable drug interactions when used in combination. In contrast, neuromodulation can be a one-time treatment that would be expected to have durable benefits to inhibit the long-term pain signal transmission and thereby achieve a favorable patient outcome.

In some embodiments, patients experiencing and/or diagnosed with chronic pain can be treated with neuromodulation alone. However, in other embodiments, patients diagnosed with diseases/conditions of the abdominal and/or reproductive viscera and experiencing chronic or intractable pain can be treated with combinations of therapies for reducing a level of perceived pain. For example, combinations of therapies can be tailored based on specific manifestations of the disease in a particular patient. In a specific example, patients having chronic pain associated with pancreatic cancer can be treated with anti-cancer therapy (e.g., chemotherapy drugs, radiation, etc.) and celiac plexus and/or superior mesenteric plexus neuromodulation. In another example, neuromodulation can be combined with pain medications (e.g., analgesics) and/or other agents (e.g., anesthetics, antidepressants, antiepileptics, narcotics, etc.).

Treatment of chronic pain or related conditions may refer to eliminating the pain, slowing the onset or rate of development of the pain, reducing the risk of developing pain typically associated with a diseased/damaged organ, preventing or delaying the development of additional symptoms associated with the chronic pain, reducing or ending symptoms associated with the chronic pain, generating a complete or partial regression of the pain, or some combination thereof.

VII. Selected Embodiments of Neuromodulation Systems and Devices

Figure 7:
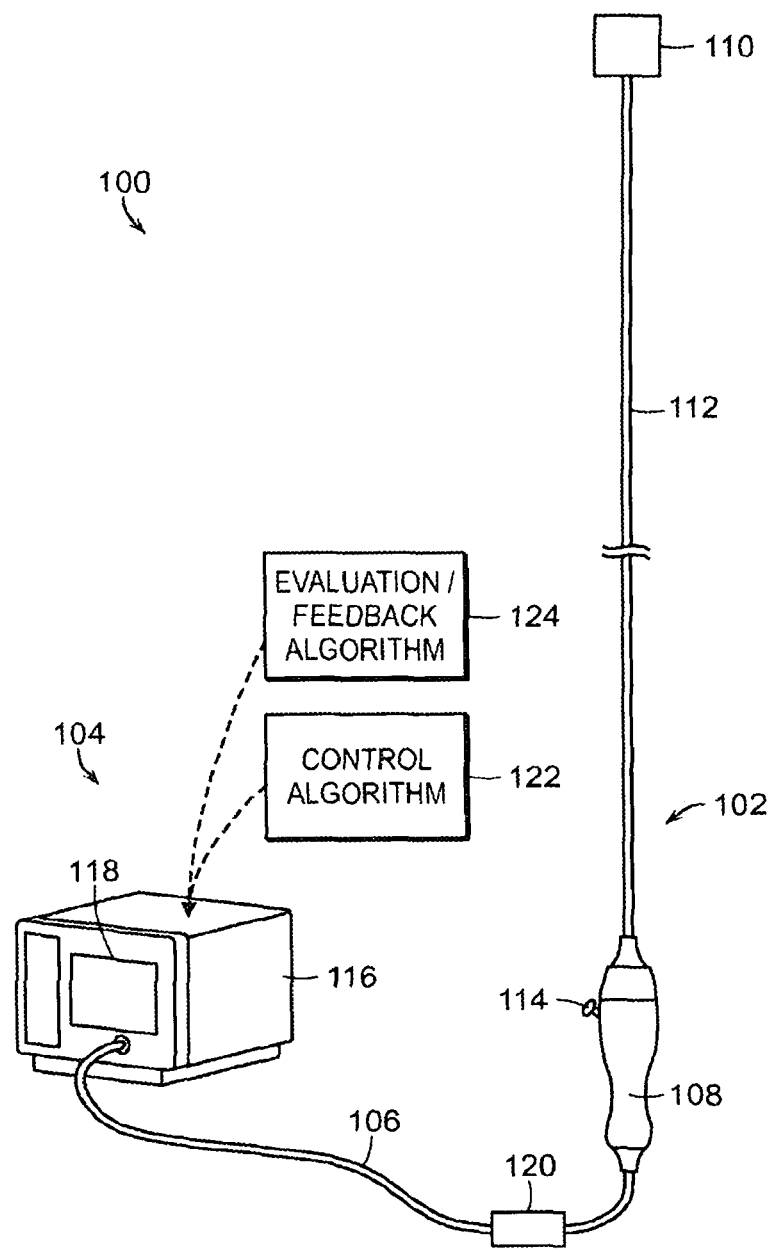
FIG. 7 illustrates an intravascular neuromodulation system configured in accordance with an embodiment of the present technology.

FIG. 7 is a partially schematic diagram illustrating a neuromodulation system 100 ("system 100") configured in accordance with an embodiment of the present technology. The system 100 can include a treatment device 102, an energy source or console 104 (e.g., a RF energy generator, a cryotherapy console, etc.), and a cable 106 extending between the treatment device 102 and the console 104. The treatment device 102 can include a handle 108, a neuromodulation assembly 110, and an elongated shaft 112 extending between the handle 108 and the neuromodulation assembly 110. The shaft 112 can be configured to locate the neuromodulation assembly 110 intravascularly at a treatment location (e.g., in or near a celiac artery, superior mesenteric artery or vein, a testicular artery or vein, a common iliac artery or vein, an internal iliac artery or vein, an external iliac artery or vein, an internal pudendal artery or vein, a superior gluteal artery or vein, deep circumflex iliac artery or vein, a vaginal artery or vein, a uterine artery or vein and/or another suitable structure for the management or treatment of pain associated with the abdominal or reproductive viscera), and the neuromodulation assembly 110 can be configured to provide or support therapeutically-effective neuromodulation at the treatment location. In some embodiments, the shaft 112 and the neuromodulation assembly 110 can be 3, 4, 5, 6, or 7 French or another suitable size. Furthermore, the shaft 112 and the neuromodulation assembly 110 can be partially or fully radiopaque and/or can include radiopaque markers corresponding to measurements, e.g., every 5 cm.

Intravascular delivery can include percutaneously inserting a guide wire (not shown) within the vasculature and moving the shaft 112 and the neuromodulation assembly 110 along the guide wire until the neuromodulation assembly 110 reaches the treatment location. For example, the shaft 112 and the neuromodulation assembly 110 can include a guide-wire lumen (not shown) configured to receive the guide wire in an over-the-wire (OTW) or rapid-exchange (RX) configuration. Other body lumens (e.g., ducts or internal chambers) can be treated, for example, by non-percutaneously passing the shaft 112 and neuromodulation assembly 110 through externally accessible passages of the body or other suitable methods. In some embodiments, a distal end of the neuromodulation assembly 110 can terminate in an atraumatic rounded tip or cap (not shown). The treatment device 102 can also be a steerable or non-steerable catheter device (e.g., a guide catheter) configured for use without a guide wire.

The neuromodulation assembly 110 can have a single state or configuration, or it can be convertible between a plurality of states or configurations. For example, the neuromodulation assembly 110 can be configured to be delivered to the treatment location in a delivery state and to provide or support therapeutically-effective neuromodulation in a deployed state. In these and other embodiments, the neuromodulation assembly 110 can have different sizes and/or shapes in the delivery and deployed states. For example, the neuromodulation assembly 110 can have a low-profile configuration in the delivery state and an expanded configuration in the deployed state. In another example, the neuromodulation assembly 110 can be configured to deflect into contact with a vessel wall in a delivery state. The neuromodulation assembly 110 can be converted (e.g., placed or transformed) between the delivery and deployed states via remote actuation, e.g., using an actuator 114 of the handle 108. The actuator 114 can include a knob, a pin, a lever, a button, a dial, or another suitable control component. In other embodiments, the neuromodulation assembly 110 can be transformed between the delivery and deployed states using other suitable mechanisms or techniques.

In some embodiments, the neuromodulation assembly 110 can include an elongated member (not shown) that can be configured to curve (e.g., arch) in the deployed state, e.g., in response to movement of the actuator 114. For example, the elongated member can be at least partially helical/spiral in the deployed state. In other embodiments, the neuromodulation assembly 110 can include a balloon (not shown) that can be configured to be at least partially inflated in the deployed state. An elongated member, for example, can be well suited for carrying one or more heating elements, electrodes or transducers and for delivering heat, electrode-based or transducer-based treatment. A balloon, for example, can be well suited for containing refrigerant (e.g., during or shortly after liquid-to-gas phase change) and for delivering cryotherapeutic treatment. A balloon can also be used in some embodiments for carrying suitable RF conducting electrodes. In some embodiments, the neuromodulation assembly 110 can be configured for intravascular and/or transvascular delivery of chemicals. For example, the neuromodulation assembly 110 can include one or more openings (not shown), and chemicals (e.g., drugs or other agents) can be deliverable through the openings. For transvascular delivery, the neuromodulation assembly 110 can include one or more needles (not shown) (e.g., retractable needles) and the openings can be at end portions of the needles.

The console 104 is configured to control, monitor, supply, or otherwise support operation of the treatment device 102. In some embodiments, the console 104 can be separate from and in communication with the treatment device 102. In other embodiments, the console 104 can be contained within or be a component of the treatment device 102. In still further embodiments, the treatment device 102 can be self-contained and/or otherwise configured for operation without connection to the console 104. As shown in FIG. 7, the console 104 can include a primary housing 116 having a display 118. The system 100 can include a control device 120 along the cable 106 configured to initiate, terminate, and/or adjust operation of the treatment device 102 directly and/or via the console 104. In other embodiments, the system 100 can include another suitable control mechanism. For example, the control device 120 can be incorporated into the handle 108. The console 104 can be configured to execute an automated control algorithm 122 and/or to receive control instructions from an operator. Furthermore, console 104 can be configured to provide feedback to an operator before, during, and/or after a treatment procedure via the display 118 and/or an evaluation/feedback algorithm 124. In some embodiments, the console 104 can include a processing device (not shown) having processing circuitry, e.g., a microprocessor. The processing device can be configured to execute stored instructions relating to the control algorithm 122 and/or the evaluation/feedback algorithm 124. Furthermore, the console 104 can be configured to communicate with the treatment device 102, e.g., via the cable 106. For example, the neuromodulation assembly 110 of the treatment device 102 can include a sensor (not shown) (e.g., a recording electrode, a temperature sensor, a pressure sensor, or a flow rate sensor) and a sensor lead (not shown) (e.g., an electrical lead or a pressure lead) configured to carry a signal from the sensor to the handle 108. The cable 106 can be configured to carry the signal from the handle 108 to the console 104.

The console 104 can have different configurations depending on the treatment modality of the treatment device 102. For example, when the treatment device 102 is configured for electrode-based or transducer-based treatment, the console 104 can include an energy generator (not shown) configured to generate RF energy, pulsed RF energy, microwave energy, optical energy, ultrasound energy (e.g., intravascularly delivered ultrasound, extracorporeal ultrasound, HIFU), direct heat energy, magnetic energy, radiation (e.g., infrared, visible, gamma), or another suitable type of energy. In some embodiments, for example, the console 104 can include a RF generator operably coupled to one or more electrodes (not shown) of the neuromodulation assembly 110.

When the treatment device 102 is configured for cryotherapeutic treatment, the console 104 can include a refrigerant reservoir (not shown) and can be configured to supply the treatment device 102 with refrigerant, e.g., pressurized refrigerant in liquid or substantially liquid phase. Similarly, when the treatment device 102 is configured for chemical-based treatment, the console 104 can include a chemical reservoir (not shown) and can be configured to supply the treatment device 102 with one or more chemicals. In some embodiments, the treatment device 102 can include an adapter (not shown) (e.g., a Lucy lock) configured to be operably coupled to a syringe (not shown). The adapter can be fluidly connected to a lumen (not shown) of the treatment device 102, and the syringe can be used, for example, to manually deliver one or more chemicals to the treatment location, to withdraw material from the treatment location, to inflate a balloon (not shown) of the neuromodulation assembly 110, to deflate a balloon of the neuromodulation assembly 110, or for another suitable purpose. In other embodiments, the console 104 can have other suitable configurations.

In certain embodiments, a neuromodulation device for use in the methods disclosed herein may combine two or more energy modalities. For example, the device may include both a hyperthermic source of ablative or modulating energy and a hypothermic source, making it capable of, for example, performing both RF neuromodulation and cryo-neuromodulation. The distal end of the treatment device may be straight (for example, a focal catheter), expandable (for example, an expanding mesh or cryoballoon), or have any other configuration (e.g., a helical coil). Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

VIII. Selected Examples of Treatment Procedures for Neuromodulation

Referring back to FIGS. 2A-5, in some embodiments the shaft(s) 24 or 36 and the therapeutic element(s) 26 or 38 can be portions of a treatment device at least partially corresponding to the treatment device 102 shown in FIG. 7. The therapeutic element(s) 26 or 38, for example, can be configured to radially expand into a deployed state at the treatment location. In the deployed state, the therapeutic element(s) 26 or 38 can be configured to contact an inner wall of a vessel of the target vasculature and to form a suitable lesion or pattern of lesions without the need for repositioning. For example, the therapeutic element(s) 26 or 38 can be configured to form a single lesion or a series of lesions, e.g., overlapping or non-overlapping. In some embodiments, the lesion or pattern of lesions can extend around generally the entire circumference of the vessel, but can still be non-circumferential at longitudinal segments or zones along a lengthwise portion of the vessel. This can facilitate precise and efficient treatment with a low possibility of vessel stenosis. In other embodiments, the therapeutic element(s) 26 or 38 can be configured form a partially-circumferential lesion or a fully-circumferential lesion at a single longitudinal segment or zone of the vessel. During treatment, the therapeutic element(s) 26 or 38 can be configured for partial or full occlusion of a vessel. Partial occlusion can be useful, for example, to reduce ischemia, while full occlusion can be useful, for example, to reduce interference (e.g., warming or cooling) caused by blood flow through the treatment location. In some embodiments, the therapeutic element(s) 26 or 38 can be configured to cause therapeutically-effective neuromodulation (e.g., using ultrasound energy) without contacting a vessel wall.

A variety of other suitable treatment locations are also possible in and around the target artery, the target vein, and/or other suitable structures. In a specific example, since the testicular artery 32 becomes narrower and more tortuous further from the aorta, it can be more convenient in some cases to treat the testicular artery 32 at its trunk. Furthermore, a treatment procedure can include treatment at any suitable number of treatment locations, e.g., a single treatment location, two treatment locations, or more than two treatment locations. In some embodiments, different treatment locations can correspond to different portions of the target artery, the target vein, and/or other suitable structures proximate tissue having relatively high concentrations of targeted sympathetic nerves (e.g., afferent nerve fibers associated with a diseased or damaged organ). The shaft(s) 24 or 36 can be steerable (e.g., via one or more pull wires, a steerable guide or sheath catheter, etc.) and can be configured to move the therapeutic element(s) 26 or 38 between treatment locations. At each treatment location, the therapeutic element(s) 26 or 38 can be activated to cause modulation of nerves proximate the treatment location. Activating the therapeutic element(s) 26 or 38 can include, for example, heating, cooling, stimulating, or applying another suitable treatment modality at the treatment location. Activating the therapeutic element(s) 26 or 38 can further include applying various energy modalities at varying power levels, intensities and for various durations for achieving modulation of nerves proximate the treatment location. In some embodiments, power levels, intensities and/or treatment duration can be determined and employed using various algorithms for ensuring modulation of nerves at select distances (e.g., depths) away from the treatment location. Furthermore, as noted previously, in some embodiments, the therapeutic element(s) 26 or 38 can be configured to introduce (e.g., inject) a chemical (e.g., a drug or other agent) into target tissue at the treatment location. Such chemicals or agents can be applied at various concentrations depending on treatment location and the relative depth of the target nerves.

The therapeutic element(s) 26 or 38 can be positioned at a treatment location within the target artery, for example, via a catheterization path including a femoral artery and the aorta, a catheterization path including the internal iliac artery, the external iliac artery or any vascular branches from these arteries, or another suitable catheterization path, e.g., a radial or brachial catheterization path. Catheterization can be guided, for example, using imaging, e.g., magnetic resonance, computed tomography, fluoroscopy, ultrasound, intravascular ultrasound, optical coherence tomography, or another suitable imaging modality. The therapeutic element(s) 26 or 38 can be configured to accommodate the anatomy of the target artery, the target vein, and/or another suitable structure. For example, the therapeutic element(s) 26 or 38 can include a balloon (not shown) configured to inflate to a size generally corresponding to the internal size of the target artery, the target vein, and/or another suitable structure. In some embodiments, the therapeutic element(s) 26 or 38 can be an implantable device and a treatment procedure can include locating the therapeutic element(s) 26 or 38 at the treatment location using the shaft(s) 24 or 36, fixing the therapeutic element(s) 26 or 38 at the treatment location, separating the therapeutic element(s) 26 or 38 from the shaft(s) 24 or 36, and withdrawing the shaft(s) 24 or 36. Other treatment procedures for modulation of sympathetic nerves in accordance with embodiments of the present technology are also possible. For example, in some embodiments, a non-ablative and/or non-neuromodulating amount of energy could be applied to simulate or re-create a patient's pain symptoms thereby allowing treating clinicians to beneficially position the device prior to delivering modulating energy. In another embodiment, nerve signals can be temporarily blocked prior to delivery of neuromodulating energy using, for example, anesthetic drugs, electrical overdrive pacing to exhaust nerve signals, etc., to temporarily abolish or diminish the pain sensation in order to determine if the device is positioned correctly.

Figure 8:
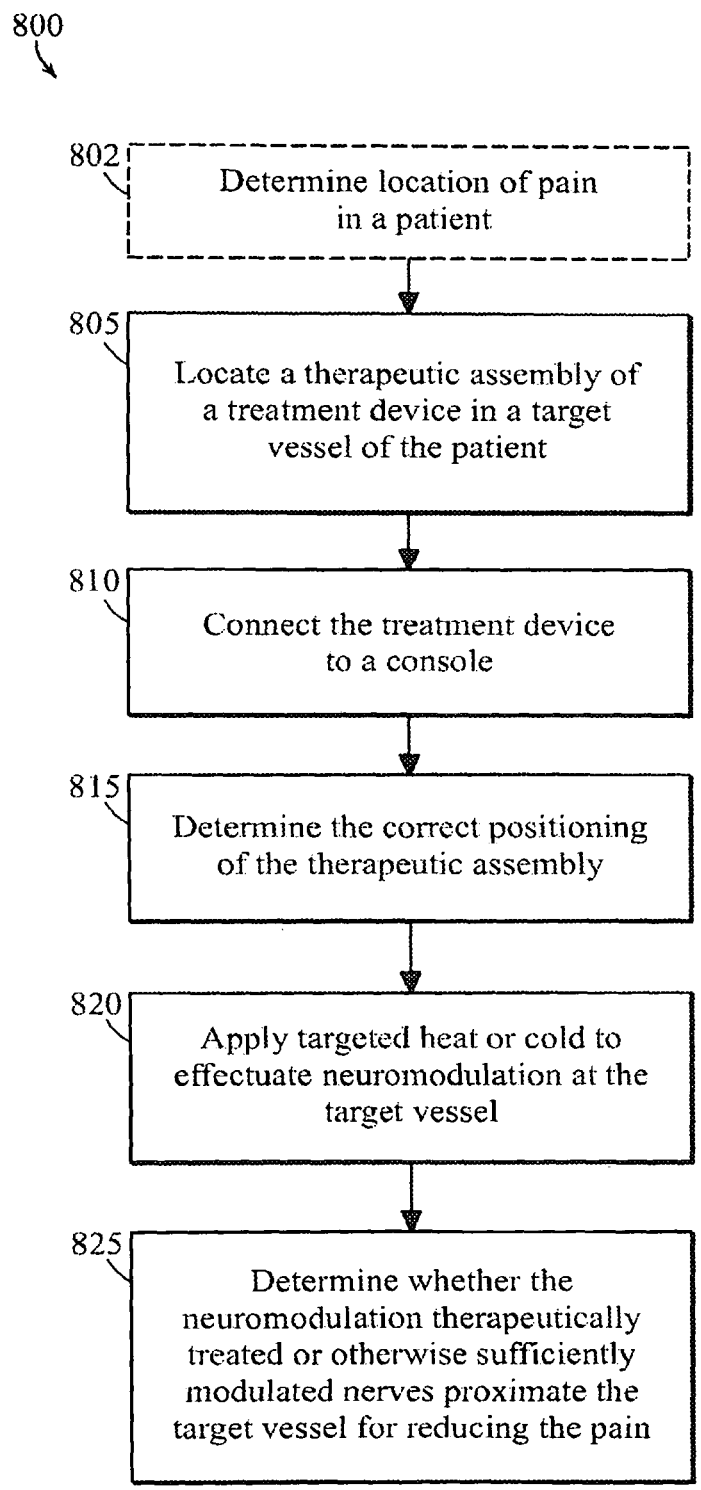
FIG. 8 is a block diagram illustrating a method of modulating target sympathetic nerves in accordance with an embodiment of the present technology.

FIG. 8 is a block diagram illustrating a method 800 of modulating sympathetic nerves using the system 100 described above with reference to FIGS. 2A-5 and 7. With reference to FIGS. 2A-5, 7, and 8 together, the method 800 can optionally include determining the location of pain in a patient (if not yet determined) and/or selecting a suitable patient for performing neuromodulation (block 802). The method 800 can include intravascularly locating the neuromodulation assembly 110 in a delivery state (e.g., low-profile configuration) at a first target site in or near a target blood vessel (e.g., a celiac artery, superior mesenteric artery or vein, a testicular artery or vein, a common iliac artery or vein, an internal iliac artery or vein, an external iliac artery or vein, an internal pudendal artery or vein, a superior gluteal artery or vein, deep circumflex iliac artery or vein, a vaginal artery or vein, a uterine artery or vein and/or another suitable structure) (block 805). The treatment device 102 and/or portions thereof (e.g., the neuromodulation assembly 110) can be inserted into a guide catheter or sheath to facilitate intravascular delivery of the neuromodulation assembly 110. In certain embodiments, for example, the treatment device 102 can be configured to fit within an 8 Fr guide catheter or smaller (e.g., 7 Fr, 6 Fr, etc.) to access small peripheral vessels. A guide wire (not shown), if present, can be used to manipulate and enhance control of the shaft 112 and the neuromodulation assembly 110 (e.g., in an over-the-wire or a rapid-exchange configuration). In some embodiments, radiopaque markers and/or markings on the treatment device 102 and/or the guide wire can facilitate placement of the neuromodulation assembly 110 at the target site (e.g., a target vessel of a patient with chronic pain). In some embodiments, a contrast material can be delivered distally beyond the neuromodulation assembly 110, and fluoroscopy and/or other suitable imaging techniques can be used to aid in placement of the neuromodulation assembly 110 at the target site.

The method 800 can further include connecting the treatment device 102 to the console 104 (block 810), and determining whether the neuromodulation assembly 110 is in the correct position at the target site and/or whether the neuromodulation assembly (e.g., electrodes or cryotherapy balloon) is functioning properly (block 815). Once the neuromodulation assembly 110 is properly located at the target site and no malfunctions are detected, the console 104 can be manipulated to initiate application of an energy field to the target site to cause electrically-induced and/or thermally-induced modulation of target sympathetic nerves near the target vessel (e.g., using electrodes or cryotherapeutic devices). Accordingly, heating and/or cooling of the neuromodulation assembly 110 causes modulation of sympathetic nerves (e.g., afferent nerve fibers transmitting pain signals) at the target site to reduce or diminish pain transmitting signals via sympathetic nerve fibers associated with the target site (block 820).

In one example, the treatment device 102 can be an RF energy emitting device and RF energy can be delivered through energy delivery elements or electrodes to one or more locations along the inner wall of the target vessel for predetermined periods of time (e.g., 120 seconds). In some embodiments, multiple treatments (e.g., 4-6) may be administered in multiple target vessel locations to achieve a desired coverage. For example, the target vessel can be a first target vessel (e.g., a first testicular artery) and the treatment procedure can include modulating nerves associated with a second target vessel (e.g., a second testicular artery) for the treatment of pain associated with the testes. In another example, pain associated with conditions of the pancreas (e.g., pancreatitis, pancreatic cancer) can include modulating nerves (e.g., celiac plexus) associated with a first target vessel (e.g., a celiac artery) and can include modulating nerves (e.g., superior mesenteric plexus) associated with a second target vessel (e.g., a superior mesenteric artery).

An objective of a treatment may be, for example, to heat tissue to a desired depth (e.g., at least about 3 mm) to a temperature (e.g., about 65° C.) that would modulate one or more nerve fibers associated with or adjacent to one or more lesions formed in the vessel wall. A clinical objective of the procedure typically is to neuromodulate a sufficient number of sympathetic nerves (e.g., afferent nerves) to reduce or diminish pain transmitting signals and/or to cause a reduction in sympathetic tone or drive to the organ(s) without, for example, disrupting organ function and while minimizing vessel trauma. If the objective of a treatment is met (e.g., tissue is heated to about 65° C. to a depth of about 3 mm) the probability of modulating nerve tissue (e.g., altering nerve function) is high. In some embodiments, a single neuromodulation treatment procedure can provide for sufficient modulation of target sympathetic nerves (e.g., modulation of a sufficient number of nerve fibers) to provide a desired clinical outcome. In other embodiments, more than one treatment may be beneficial for modulating a desired number or volume of target sympathetic nerve fibers, and thereby achieve clinical success. The greater the number of technically successful treatments, the greater the probability of modulating a sufficient proportion of target sympathetic nerves, and thus the greater the probability of clinical success. In other embodiments, an objective may include reducing or eliminating target sympathetic nerve function completely.

In a specific example of using RF energy for sympathetic nerve modulation, a clinician can commence treatment which causes the control algorithm 122 (FIG. 7) to initiate instructions to the generator (not shown) to gradually adjust its power output to a first power level (e.g., 5 watts) over a first time period (e.g., 15 seconds). The power increase during the first time period is generally linear. As a result, the generator increases its power output at a generally constant rate of power/time, i.e., in a linear manner. Alternatively, the power increase may be non-linear (e.g., exponential or parabolic) with a variable rate of increase. Once the first power level and the first time are achieved, the algorithm may hold at the first power level until a second predetermined period of time has elapsed (e.g., 3 seconds). At the conclusion of the second period of time, power is again increased by a predetermined increment (e.g., 1 watt) to a second power level over a third predetermined period of time (e.g., 1 second). This power ramp in predetermined increments of about 1 watt over predetermined periods of time may continue until a maximum power $P_{MAX}$ is achieved or some other condition is satisfied. In one embodiment, $P_{MAX}$ is 8 watts. In another embodiment, $P_{MAX}$ is 10 watts, or in a further embodiment, $P_{MAX}$ is 6.5 watts. In some embodiments, $P_{MAX}$ can be about 6 watts to about 10 watts. Optionally, the power may be maintained at the maximum power $P_{MAX}$ for a desired period of time or up to the desired total treatment time (e.g., up to about 120 seconds) or until a specified temperature is reached or maintained for a specified time period.

In another specific example, the treatment device 102 can be a cryogenic device and cryogenic cooling can be applied for one or more cycles (e.g., for 30 second increments, 60 second increments, 90 second increments, etc.) in one or more locations along the circumference and/or length of the target vessel. The cooling cycles can be, for example, fixed periods or can be fully or partially dependent on detected temperatures (e.g., temperatures detected by a thermocouple (not shown) of the neuromodulation assembly 110). In some embodiments, a first stage can include cooling tissue until a first target temperature is reached. A second stage can include maintaining cooling for a set period, such as 15-180 seconds (e.g., 90 seconds). A third stage can include terminating or decreasing cooling to allow the tissue to warm to a second target temperature higher than the first target temperature. A fourth stage can include continuing to allow the tissue to warm for a set period, such as 10-120 seconds (e.g., 60 seconds). A fifth stage can include cooling the tissue until the first target temperature (or a different target temperature) is reached. A sixth stage can include maintaining cooling for a set period, such as 15-180 seconds (e.g., 90 seconds). A seventh stage can, for example, include allowing the tissue to warm completely (e.g., to reach a body temperature).

After providing the therapeutically-effective neuromodulation energy (e.g., cryogenic cooling, RF energy, ultrasound energy, direct heat, etc.), the method 800 may also include determining whether the neuromodulation therapeutically treated the patient for management of pain or otherwise sufficiently modulated nerves or other neural structures proximate the target site(s) for reducing pain (block 825). For example, the process of determining whether the neuromodulation therapeutically treated the nerves can include determining whether nerves were sufficiently modulated or otherwise disrupted to reduce, suppress, inhibit, block or otherwise affect the afferent and/or efferent signals, such as pain signals (e.g., by evaluation of suitable biomarkers, stimulation and recording of nerve signals, etc.). In a further embodiment, patient assessment could be performed at tune intervals (e.g., 1 month, 3 months, 6 months, 12 months) following neuromodulation treatment. For example, patient can be assessed for measurements of perceived pain using one or more pain measurement scales (FIGS. 1A-1E), and measures of sympathetic activity (e.g., MSNA, and/or norepinephrine spillover to plasma, whole body norepinephrine spillover, and heart rate variability).

In other embodiments, various steps in the method 800 can be modified, omitted, and/or additional steps may be added. In further embodiments, the method 800 can have a delay between applying therapeutically-effective neuromodulation energy at a first target site at or near a first target vessel and applying therapeutically-effective neuromodulation energy at a second target site at or near a second target vessel. For example, neuromodulation of the first testicular artery can take place at a first treatment session, and neuromodulation of the second testicular artery can take place a second treatment session at a later time.

As discussed previously, treatment procedures for modulation of sympathetic nerves in accordance with embodiments of the present technology are expected to improve at least one aspect associated with perceived pain (e.g., pain caused by disease or damage to an abdominal or reproductive organ). For example, with respect to chronic pain associated with the abdominal or reproductive viscera, modulation of sympathetic nerves at an appropriate target vessel as disclosed herein and in accordance with embodiments of the present technology is expected to reduce a perceived intensity of pain, change a quality of pain, or increase physical or mental function/ability of a patient experiencing pain. In a particular example, the intensity level of pain in a patient is expected to be reduced at least about 5% within about three months after modulating the sympathetic nerves associated with the damaged or diseased organ in the patient that is believed to be the cause of the pain. These and other clinical effects are expected to be detectable immediately after a treatment procedure or after a delay, e.g., of 1, 2, or 3 months. In some instances, it may be useful to repeat neuromodulation at the same treatment location or a different treatment location after a suitable delay, e.g., 1, 2, or 3 years. In still other embodiments, however, other suitable treatment regimens or techniques may be used.

IX. Pertinent Anatomy and Physiology

The following discussion provides further details regarding pertinent patient anatomy and physiology. This section is intended to supplement and expand upon the previous discussion regarding the relevant anatomy and physiology, and to provide additional context regarding the disclosed technology and the therapeutic benefits associated with neuromodulation for the treatment and management of pain associated with the abdominal and/or reproductive viscera.

A. The Sympathetic Nervous System

The SNS is a branch of the autonomic nervous system along with the enteric nervous system and parasympathetic nervous system. It is always active at a basal level (called sympathetic tone) and becomes more active during times of stress. Like other parts of the nervous system, the SNS operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine binds adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The SNS is responsible for up- and down-regulation of many homeostatic mechanisms in living organisms. Fibers from the SNS innervate tissues in almost every organ system, providing at least some regulatory function to physiological features as diverse as pupil diameter, gut motility, and urinary output. This response is also known as the sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the SNS and indirectly via catecholamines secreted from the adrenal medulla.

Science typically looks at the SNS as an automatic regulation system, that is, one that operates without the intervention of conscious thought. Some evolutionary theorists suggest that the SNS operated in early organisms to maintain survival as the SNS is responsible for priming the body for action. One example of this priming is in the moments before waking, in which sympathetic outflow spontaneously increases in preparation for action.

1. The Sympathetic Chain

Figure 9:
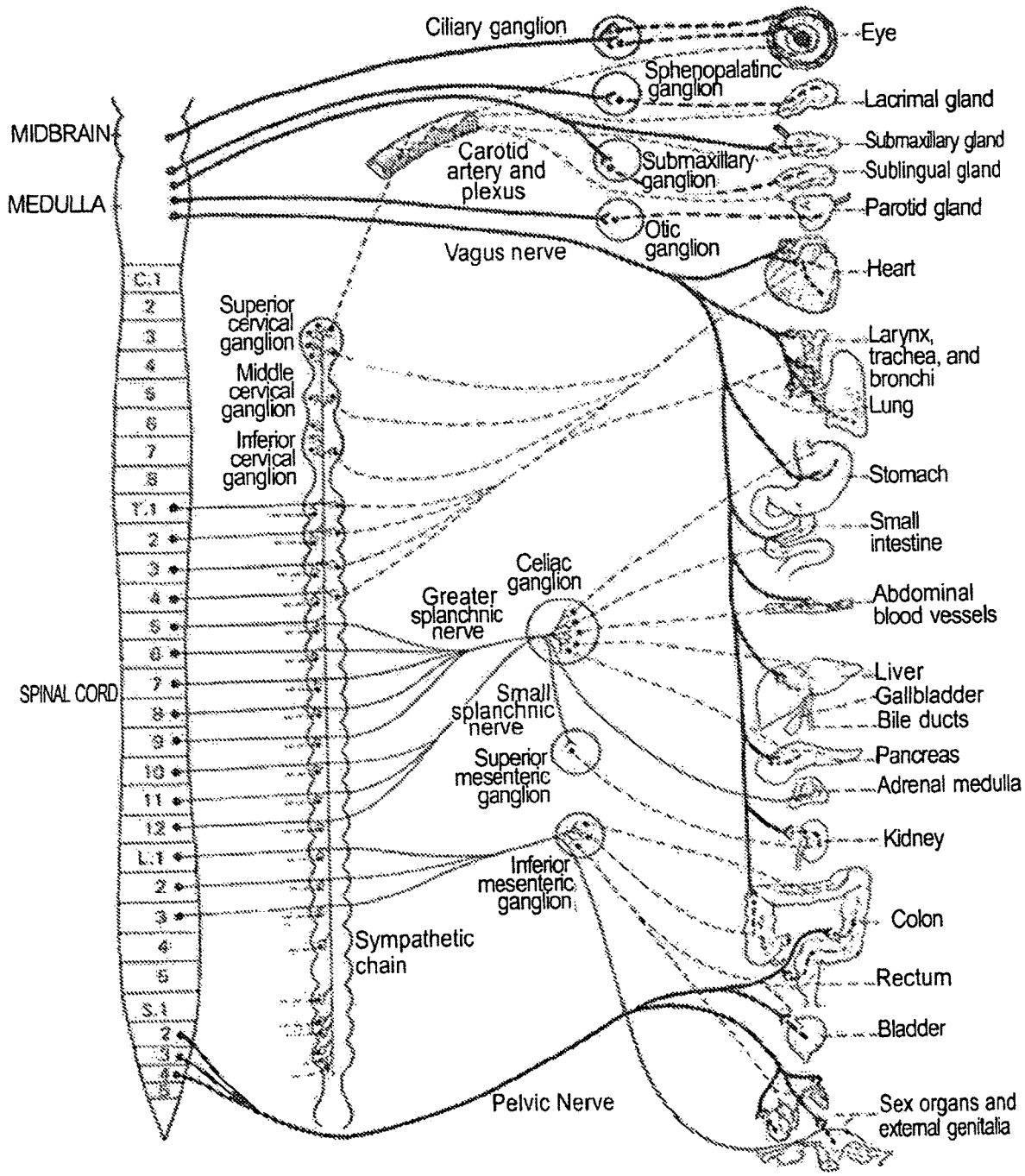
FIG. 9 is a conceptual illustration of the sympathetic nervous system (SNS) and how the brain communicates with the body via the SNS.

As shown in FIG. 9, the SNS provides a network of nerves that allows the brain to communicate with the body. Sympathetic nerves originate inside the vertebral column, toward the middle of the spinal cord in the intermodiolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors that connect to either the paravertebral (which lie near the vertebral column) or prevertebral (which lie near the aortic bifurcation) ganglia extending alongside the spinal column.

In order to reach the target organs and glands, the axons travel long distances in the body. Many axons relay their message to a second cell through synaptic transmission. The first cell (the presynaptic cell) sends a neurotransmitter across the synaptic cleft (the space between the axon terminal of the first cell and the dendrite of the second cell) where it activates the second cell (the postsynaptic cell). The message is then propagated to the final destination.

In the SNS and other neuronal networks of the peripheral nervous system, these synapses are located at sites called ganglia, discussed above. The cell that sends its fiber to a ganglion is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands. The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Organ Innervation

The abdominal organs are innervated by the celiac plexus and the superior mesenteric plexus or ganglion (FIGS. 2A and 2B), a network of nerve fibers accompanying the abdominal vessels. The celiac ganglion, aorticorenal ganglion, the phrenic plexus, the hepatic plexus, the inferior gastric plexus, the lineal plexus, the superior gastric plexus, the suprarenal plexus, the renal plexus, the spermatic plexus, the superior mesenteric plexus, the abdominal aortic plexus, and the inferior mesenteric plexus are all subsidiaries of the celiac plexus and provide innervation to much of the abdominal and reproductive viscera. The pelvis plexuses supply the viscera the pelvic cavity (e.g., the uterine plexus, the vaginal plexus).

3. Sympathetic Neural Activity

Messages travel through the SNS in a bidirectional flow. Efferent messages may trigger changes in different parts of the body simultaneously. For example, the SNS may accelerate heart rate; widen bronchial passages; decrease motility (movement) of the large intestine; constrict blood vessels; increase peristalsis in the esophagus; cause pupil dilation, cause piloerection (i.e., goose bumps), cause perspiration (i.e., sweating), and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing overactivity of the SNS.

As mentioned above, the sympathetic nerve fibers, and in particular, the afferent nerve fibers carry and/or transmit pain signals from nociceptors (e.g., pain receptors) in a damaged or diseased organ (e.g., pancreas, liver, testes, vulva, etc.) or body structure (e.g., pelvis) via the pelvis plexus network or the celiac plexus network and to the spinal cord and then to the thalamus and cortex of the brain, thereby inducing the sensation of pain. Typically, nociceptive pain is caused by stimulation of these sympathetic nerve fibers only when a threshold intensity (e.g., a harmful intensity) is achieved within the tissue.

X. Further Examples

1. A method of treating a human patient having chronic pain associated with a disease or condition of a pancreas, liver, biliary tract, gallbladder, spleen, stomach, small intestine colon or of an abdominal visceral artery, the method comprising:
  intravascularly positioning a neuromodulation assembly within a target blood vessel of the patient and adjacent to a target sympathetic nerve of the patient; and
  reducing sympathetic neural activity in the patient by delivering energy to the target sympathetic nerve via the neuromodulation assembly to modulate a function of the target sympathetic nerve,
  wherein reducing sympathetic neural activity improves a perceived pain associated with the disease or condition of the patient.

2. A method of treating a human patient having chronic pain associated with a disease or condition of the reproductive system, the method comprising:
  intravascularly positioning a neuromodulation assembly within a target blood vessel of the patient and adjacent to a target sympathetic nerve of the reproductive system of the patient; and
  reducing sympathetic neural activity in the patient by delivering energy to the target sympathetic nerve via the neuromodulation assembly to modulate a function of the target sympathetic nerve,
  wherein reducing sympathetic neural activity improves a perceived pain associated with the disease or condition of the patient.

3. The method of example 1 or example 2 wherein reducing sympathetic neural activity in the patient in a manner that improves a perceived pain by the patient comprises reducing a level of pain as reported on a pain scale.

4. The method of example 3 wherein the pain scale is a standardized Visual Analog Scale (VAS), and wherein a post-neuromodulation VAS score of the patient is less than a pre-neuromodulation VAS-score of the patient.

5. The method of example 3 wherein the pain scale is at least one of a standardized Visual Analog Scale, a graphic faces pain scale, a Wong-Baker FACES Pain Rating Scale, a colored analogue scale, a Face Legs Arms Cry Consolability Scale, a word descriptor scale, a verbal scale and a functional pain scale.

6. The method of any one of examples 1-5 wherein reducing sympathetic neural activity improves a perceived pain by the patient by at least about 5%.

7. The method of any one of examples 1-6 wherein reducing sympathetic neural activity improves a perceived pain by the patient by at least about 20% within about three months to about 12 months after reducing sympathetic neural activity in the patient by delivering energy to the target sympathetic nerve.

8. The method of any one of examples 1-7 wherein reducing sympathetic neural activity improves at least one of a perceived pain intensity level, a quality of pain, a level of physical function of the patient, and a level of mental function of the patient.

9. The method of any one of examples 1 or 3-8 wherein the chronic pain is associated with a disease or condition comprising pancreatitis or pancreatic cancer.

10. The method of any one of examples 1 or 3-9 wherein intravascularly positioning a neuromodulation assembly within a target blood vessel of the patient includes positioning a neuromodulation assembly within a celiac artery.

11. The method of any one of examples 1 or 3-10 wherein intravascularly positioning a neuromodulation assembly within a target blood vessel of the patient includes positioning a neuromodulation assembly within a superior mesenteric artery.

12. The method of any one of examples 2-8 wherein the chronic pain is associated with a testicle of the patient.

13. The method of any one of examples 2-8 or 12 wherein intravascularly positioning a neuromodulation assembly within a target blood vessel of the patient includes positioning a neuromodulation assembly within a testicular artery.

14. The method of any one of examples 2-8, 12, or 13 wherein the target sympathetic nerve is a testicular afferent nerve.

15. The method of any one of examples 2-8 wherein the chronic pain is associated with the vulva, vagina and/or clitoris.

16. The method of any one of examples 2-8 or 12-15 wherein intravascularly positioning a neuromodulation assembly within a target blood vessel of the patient includes positioning a neuromodulation assembly within an external iliac artery, an interior iliac artery, or an internal pudendal artery.

17. The method of example 15 wherein the target sympathetic nerve resides in the vaginal plexus, and wherein intravascularly positioning a neuromodulation assembly within a target blood vessel of the patient includes positioning a neuromodulation assembly within a vaginal artery.

18. The method of any one of examples 1-17 wherein reducing sympathetic neural activity in the patient by delivering energy to the target sympathetic nerve comprises at least partially inhibiting afferent neural activity.

19. The method of any one of examples 1-18 wherein reducing sympathetic neural activity in the patient by delivering energy to the target sympathetic nerve comprises thermally inducing modulation of the target sympathetic nerve of the patient via an intravascularly positioned catheter carrying one or more thermal energy delivery elements positioned at least proximate to the target sympathetic nerve.

20. The method of example 19 wherein modulating the target sympathetic nerve includes heating the target sympathetic nerve from within the target blood vessel of the patient via the one or more thermal energy delivery elements.

21. The method of example 20 wherein thermally modulating the target sympathetic nerve includes cryotherapeutically cooling the target sympathetic nerve via the one or more thermal energy delivery elements.

22. The method of example 20 wherein thermally modulating the target sympathetic nerve includes delivering ultrasound energy to the target sympathetic nerve.

23. The method of any one of examples 1 or 3-8 wherein the chronic pain is associated with visceral artery insufficiency.

24. The method of any one of examples 1 or 3-8 wherein the chronic pain is associated with a hepatobiliary disease.

25. A method, comprising:
  percutaneously introducing a neuromodulation assembly at a distal portion of a treatment device proximate to neural fibers innervating a damaged or diseased organ of a human patient diagnosed with chronic or debilitating pain, wherein the damaged or diseased organ comprises at least one of a pancreas, liver, biliary tract, gallbladder, spleen, stomach, small intestine, colon or a reproductive organ;

partially disrupting function of at least afferent neural fibers innervating the organ by applying thermal energy to the neural fibers via the neuromodulation assembly; and removing the neuromodulation assembly from the patient after treatment, wherein partial disruption of the function of at least the afferent neural fibers innervating the organ therapeutically treats the chronic or debilitating pain.

26. The method of example 25 wherein the patient is diagnosed with a disease of the pancreas, and wherein partial disruption of the function of at least the afferent neural fibers innervating the pancreas reduces a perceived pain level by at least about 10% in the patient.

27. The method of example 25 or example 26 wherein the neural fibers originate from the celiac plexus or the superior mesenteric plexus.

28. The method of example 25 wherein the patient is diagnosed with orchialgia, and wherein partial disruption of the function of at least the afferent neural fibers innervating a testicle reduces a perceived pain level by at least about 10% in the patient.

29. The method of example 25 or example 28 wherein the neural fibers originate from the spermatic plexus, the lumbar plexus or the sacral plexus.

30. A method for managing pain in a human patient, the method comprising:

transluminally positioning an energy delivery element of a catheter within a target blood vessel of the patient and adjacent to neural fibers that innervate a damaged or diseased pancreas, liver, biliary tract, gallbladder, spleen, stomach, small intestine, colon, abdominal visceral artery, or reproductive organ of the patient; and at least partially ablating the neural fibers innervating the organ of the patient via the energy delivery element, wherein at least partially ablating the neural fibers innervating the organ results in a therapeutically beneficial improvement in a measurable parameter associated with the pain of the patient.

31. The method of example 30, further comprising administering one or more pharmaceutical drugs to the patient, wherein the pharmaceutical drugs are selected from the group consisting of analgesics, anti-inflammatory drugs and/or anti-depressants.

32. The method of example 30 or example 31 wherein at least partially ablating the neural fibers innervating the organ of the patient via the energy delivery element comprises delivering a thermal electric field to the neural fibers via at least one electrode.

XI. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Further, in additional embodiments, the system 100 may include a treatment device configured to deliver therapeutic energy to the patient from an external location outside the patient's body, i.e., without direct or close contact to the target site. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system comprising:
a housing; and
a processing device in the housing, the processing device comprising processing circuitry and being configured to:
determine a baseline condition of a pain parameter associated with a diagnosed disease or condition of a patient,
after a target sympathetic nerve of the patient is at least partially ablated, receive a post-neuromodulation condition of the pain parameter, and
compare the post-neuromodulation condition to the baseline condition to determine a change in the pain parameter, the change in the pain parameter providing a measurable indicator of a reduction of a pain level in the patient following neuromodulation treatment.

2. The system of claim 1, wherein the processing device is further configured to control delivery of neuromodulation therapy to the patient to at least partially ablate the target sympathetic nerve.

3. The system of claim 1, wherein the diagnosed disease or condition comprises chronic pain, and wherein the pain parameter includes at least one of pain severity, pain quality, pain radiation pattern, pain duration, degree of pain level fluctuation, frequency of pain remissions, or level of function of the patient diagnosed with chronic pain.

4. The system of claim 1, wherein the pain level is associated with the diagnosed disease or condition of a pancreas, liver, biliary tract, gallbladder, spleen, stomach, small intestine, color or of an abdominal visceral artery.

5. The system of claim 1, wherein to determine the baseline condition of the pain parameter and the post-neuromodulation condition of the pain parameter, the processing circuitry is configured to receive a pain scale rating.

6. The system of claim 1, wherein the processing circuitry is configured to determine the baseline condition of the pain parameter and the post-neuromodulation condition of the pain parameter based on a sensed physiological parameter of the patient.

7. The system of claim 1, wherein to determine the baseline condition of the pain parameter and the post-neuromodulation condition of the pain parameter, the processing circuitry is configured to measure a marker of sympathetic nerve activity in the patient.

8. The system of claim 7, wherein the marker of sympathetic nerve activity comprises at least one of a plasma norepinephrine level, muscle sympathetic nerve activity, norepinephrine spillover, or heart rate variability.

9. The system of claim 1, wherein the change in the pain parameter is a decrease in sympathetic nerve activity over 1 month, 2 months, 3 months, 6 months, 9 months or 12 months post-neuromodulation.

10. The system of claim 1, further comprising:
a catheter device comprising a neuromodulation assembly; and
a console configured to control delivery of neuromodulation therapy to the patient by the neuromodulation assembly to at least partially ablate the target sympathetic nerve.

11. The system of claim 10, wherein the neuromodulation assembly is configured to deliver energy to at least partially ablate the target sympathetic nerve.

12. The system of claim 11, wherein the energy includes one of radio frequency energy, pulsed radio frequency energy, microwave energy, optical energy, ultrasound energy, cryotherapeutic energy, directed heat energy, radiation or combinations thereof.

13. The system of claim 10, wherein the neuromodulation assembly is configured to deliver cryotherapeutic treatment to at least partially ablate the target sympathetic nerve.

14. The system of claim 10, wherein the neuromodulation assembly is configured to deliver a chemical to at least partially ablate the target sympathetic nerve.

15. A system comprising:
a housing; and
a processing device in the housing, the processing device comprising processing circuitry and being configured to:
determine a baseline condition of a pain parameter associated with a diagnosed disease or condition of a patient, the pain parameter including at least one of pain severity, pain quality, pain radiation pattern, pain duration, degree of pain level fluctuation, frequency of pain remissions, or level of function of the patient diagnosed with chronic pain;
after a target sympathetic nerve of the patient is at least partially ablated, determine a post-neuromodulation condition of the pain parameter; and
compare the post-neuromodulation condition to the baseline condition to determine a change in the pain parameter, the change in the pain parameter providing a measurable indicator of a reduction of a pain level in the patient following treatment using the neuromodulation assembly.

16. The system of claim 15, wherein the processing device is further configured to control delivery of neuromodulation therapy to tissue of the patient by a neuromodulation assembly to at least partially ablate the target sympathetic nerve.

17. The system of claim 15, wherein the pain level is associated with a diagnosed disease or condition of a pancreas, liver, biliary tract, gallbladder, spleen, stomach, small intestine, color or of an abdominal visceral artery.

18. The system of claim 15, wherein to determine the baseline condition of the pain parameter and the post-neuromodulation condition of the pain parameter, the processing circuitry is configured to receive a pain scale rating.

19. The system of claim 15, wherein to determine the baseline condition of the pain parameter and the post-neuromodulation condition of the pain parameter, the processing circuitry is configured to measure a marker of sympathetic nerve activity in the patient.

20. The system of claim 19, wherein the marker of sympathetic nerve activity comprises at least one of a plasma norepinephrine level, muscle sympathetic nerve activity, norepinephrine spillover, or heart rate variability.

* * * * *